(12) United States Patent
Dewaele et al.

(10) Patent No.: US 11,457,904 B2
(45) Date of Patent: Oct. 4, 2022

(54) REDUCED DIAMETER STEERABLE INSTRUMENT

(71) Applicant: Steerable Instruments NV, Sint-Denijs-Westrem (BE)

(72) Inventors: Frank Dewaele, De Pinte (BE); Bart Blanckaert, Eeklo (BE); Cyriel Mabilde, Oudenaarde (BE); Lieven Maene, Knokke-Heist (BE); Alain Kalmar, Ghent (BE)

(73) Assignee: Steerable Instruments NV, Sint-Denijs-Westrem (BE)

( * ) Notice: Subject to any disclaimer, the term of this patent is extended or adjusted under 35 U.S.C. 154(b) by 215 days.

(21) Appl. No.: 16/763,112

(22) PCT Filed: Nov. 15, 2018

(86) PCT No.: PCT/EP2018/081436
§ 371 (c)(1),
(2) Date: May 11, 2020

(87) PCT Pub. No.: WO2019/096932
PCT Pub. Date: May 23, 2019

(65) Prior Publication Data
US 2020/0397421 A1 Dec. 24, 2020

(30) Foreign Application Priority Data
Nov. 15, 2017 (EP) .................................. 17201797

(51) Int. Cl.
*A61B 17/00* (2006.01)
*A61B 34/30* (2016.01)
*A61M 25/01* (2006.01)

(52) U.S. Cl.
CPC ............ *A61B 17/00234* (2013.01); *A61B 2017/00314* (2013.01); *A61B 2017/00327* (2013.01); *A61B 2034/301* (2016.02); *A61M 25/0147* (2013.01)

(58) Field of Classification Search
CPC ............ A61B 17/00234; A61B 17/29; A61B 2017/003; A61B 2017/00314;
(Continued)

(56) References Cited

U.S. PATENT DOCUMENTS

2005/0273085 A1  12/2005  Hinman et al.
2008/0103452 A1  5/2008  Voegele et al.
(Continued)

FOREIGN PATENT DOCUMENTS

WO    2016091856 A1    6/2016

OTHER PUBLICATIONS

International Search Report dated Feb. 20, 2019 from PCT International Patent Application No. PCT/EP2018/081436.
(Continued)

*Primary Examiner* — Mohamed G Gabr
(74) *Attorney, Agent, or Firm* — Amster, Rothstein & Ebenstein LLP

(57) ABSTRACT

A longitudinal steerable tool (100) having a proximal (20) and distal (40) end comprising a sub-region that is a proximal amplifier region, PAR, (136) wherein the LMs (110) are arranged around a fictive tube (180) exhibiting size-decremental plane sections in a distal direction, and comprising a sub-region that is a distal attenuating region, DAR, (138) wherein the LMs (110) are arranged around a fictive tube (180) exhibiting size-incremental plane sections in a distal direction. Further provided is a longitudinal steerable tool (100) having a sheath unit (430) disposed at least partially over each of a bendable proximal part (130) and/or bendable
(Continued)

distal part (134), the sheath unit (430) having less compliance in a radial direction compared with in an axial direction.

20 Claims, 9 Drawing Sheets

(58) Field of Classification Search
CPC .......... A61B 2017/00323; A61B 2017/00327; A61B 2017/291; A61B 2034/301; A61B 2034/306; A61M 25/0147
See application file for complete search history.

(56) References Cited

U.S. PATENT DOCUMENTS

| | | |
|---|---|---|
| 2012/0123327 A1 | 5/2012 | Miller |
| 2015/0150633 A1 | 6/2015 | Castro et al. |
| 2016/0302818 A1 | 10/2016 | Weisenburgh, II et al. |
| 2017/0273702 A1* | 9/2017 | Dewaele ................ A61B 17/29 |
| 2018/0146841 A1 | 5/2018 | Dewaele et al. |

OTHER PUBLICATIONS

Written Opinion dated Feb. 20, 2019 from PCT International Patent Application No. PCT/EP2018/081436.

\* cited by examiner

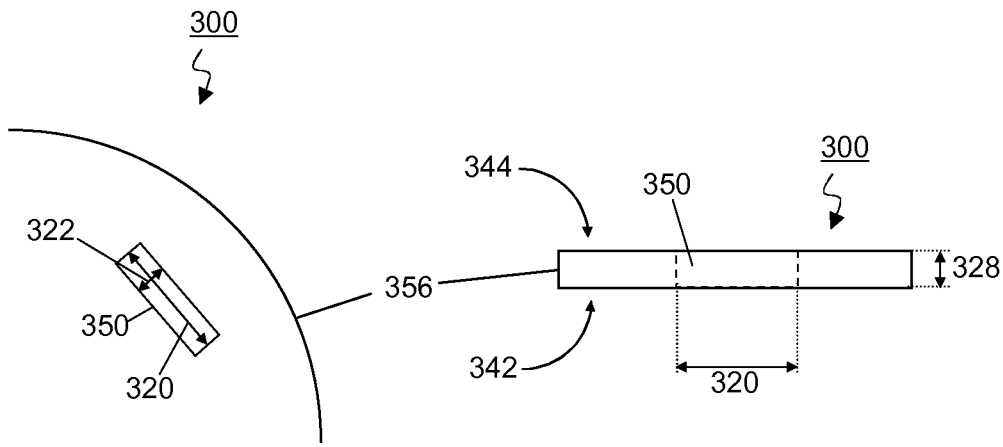
FIG. 9A  FIG. 9B
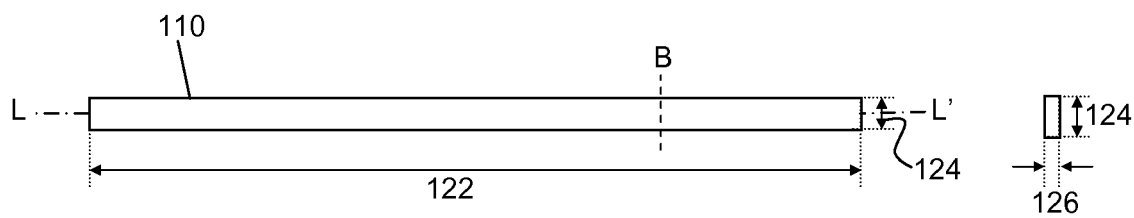
FIG. 10A  FIG. 10B
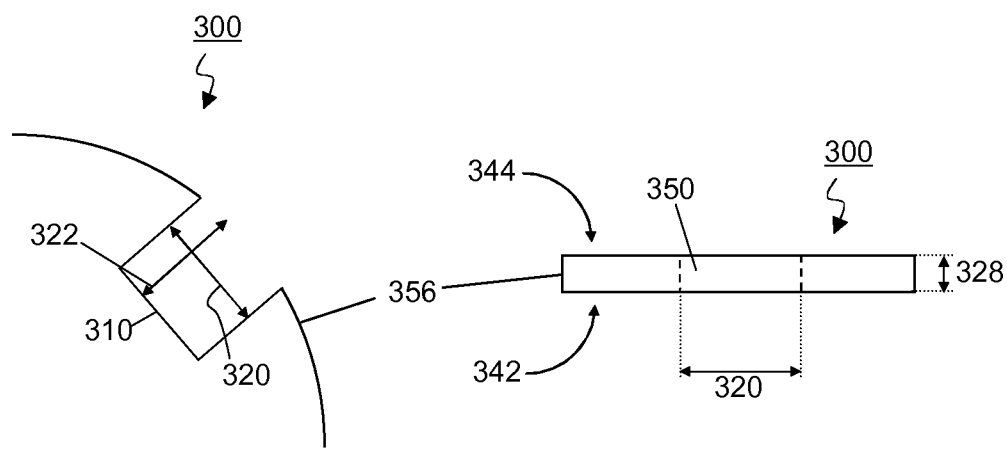
FIG. 11A  FIG. 11B

REDUCED DIAMETER STEERABLE INSTRUMENT

CROSS-REFERENCE TO RELATED APPLICATIONS

This application is a U.S. national stage entry under 35 U.S.C. § 371 of PCT International Patent Application No. PCT/EP2018/081436, filed Nov. 15, 2018, which claims priority to European Patent Application No. 17201797.2, filed Nov. 15, 2017, the contents of each of which are incorporated herein by reference in their entirety.

FIELD OF THE INVENTION

The present invention is in a field of steerable instruments for industrial, engineering and medical uses, more in particular for minimally invasive surgery. It is particularly relates to narrowed instruments.

SUMMARY

Provided is a longitudinal steerable tool (100) having a proximal (20) and distal (40) end comprising:
 a set of longitudinal members, LM, (110) arranged in a longitudinal direction, and
 a bendable proximal part (130, BPP), bendable distal part (134, BDP), and a shaft region, SR (132) between the BDP (134) and BPP (130) wherein movements of the BPP (130) are transmitted to the BDP (134) along the SR (132) by the LMs (110),
wherein the longitudinal steerable tool (100) comprises a sub-region that is a proximal amplifier region, PAR, (136) wherein the LMs (110) are arranged around a fictive tube (180) exhibiting size-decremental plane sections in a distal direction for at least 2 plane sections (182, 182') of the fictive tube (180), and
wherein the longitudinal steerable tool (100) comprises a sub-region that is a distal attenuating region, DAR, (138) wherein the LMs (110) are arranged around a fictive tube (180) exhibiting size-incremental plane sections in a distal direction for at least 2 plane sections (184, 184') of the fictive tube (180).

Consecutive plane sections of the fictive tube (180) in the PAR (136) may gradually decrease in size in the proximal (20) to the distal (40) direction, and/or
 consecutive plane sections of the fictive tube (180) in the DAR (138) may gradually increase in size in the proximal (20) to the distal (40) direction.

The PAR (136) may be located at the proximal end (20) of the SR (132) or at least partially within the BPP (130), and/or
the DAR, (138) may be located at the distal end (40) of the SR (132) or at least partially within the BDP (134).

The longitudinal steerable tool (500) may further comprise a set of LM guides (300) configured to maintain the LMs (110) at the essentially constant circumferential and radial position and slidable with respect to the fictive tube (180)

The PAR (135) may be disposed with at least two of said LM guides (316, 316a-c), and/or the DAR (138) may be disposed with at least one of said LM guides (318, 318a-c), Each LM guide (300) of the set comprises a body may be provided with a set of discrete channels (350) each accommodating one or two LMs (110), which channels are arranged around the fictive tube (180).

At least some of LM guides in the set may be articulated LM guides (316a-c, 318a-c) tandemly arranged in the BPP (130) and in the BDP (134), each articulated with respect to an adjacent articulated LM guide (316a-c, 318a-c), thereby supporting bending of the LMs (110) in the BDP (130) and in the BPP (134).

The articulated LM guides (316a-c, 318a-c) may be in pairwise mutual contact through a pivot joint.

The channels (350) of consecutive LM guides (316a-c) in the PAR (136) may decrease incrementally in distance from a central (A-A') axis of the longitudinal steerable tool (100) in the distal (40) direction, and/or
the channels (350) of consecutive LM guides (318a-c) in the DAR (138) may increase incrementally in distance from a central (A-A') axis of the longitudinal steerable tool (100) in the distal (40) direction.

One or more of the LM guides in the set may be fixed LM guides (312a-c) tandemly arranged in the SR (132) and rotationally fixed with respect to each other.

The longitudinal steerable tool (100) may be configured to move the BPP (134) and BDP (130) omni-directionally.

The fictive tube (180) in the PAR (136) may contain a truncated cone shape, the larger end disposed at the proximal (20) end, and/or
the fictive tube (180) in the DAR (134) may contain a truncated cone shape, the larger end disposed at the distal (40) end.

The BDP (134) may be configured for movement in at least two different intersecting planes responsive to the movements of the BPP (134), and
the longitudinal steerable tool (100) is further provided with an end effector (150) at the distal end of the BDP (134), and/or
 the longitudinal steerable tool (100) may be configured such that the end effector (150) is rotationally fixed in relation to the BDP (134), and the end effector is rotatable when the BDP (134) is in a bent position, by a complementary rotation of the BPP (130).

The PAR (136) and/or DAR (138) may each be provided with a set of LM guides (300) configured to maintain the LMs (110) at the essentially constant circumferential and radial position and slidable with respect to the fictive tube (180),
 each LM guide (300) in the PAR (136) and/or DAR (138) may comprise a body provided with a set of discrete channels (350) each accommodating one or two LMs (110), and being open to a circumferential edge (356) of the LM guide (300), which channels are arranged around the fictive tube (180), and
 the PAR (136) and/or DAR (138) may each provided with at least one ring of non-radially compliant material disposed in a space separating the LM guides (300), configured to retain the LMs (110) within the open edged channels (350).

The ring may be made from heat-shrink material.

Provided is a longitudinal steerable tool (100) having a proximal (20) and distal (40) end comprising:
 a set of longitudinal members, LM, (110) arranged in a longitudinal direction around a fictive tube (180) maintained at an essentially constant circumferential and radial position with respect to the fictive tube (180) and being slidable relative to the fictive tube (180), and
 a bendable proximal part (130, BPP), bendable distal part (134, BDP), and a shaft region, SR (132) between the BDP (134) and BPP (130) wherein movements of the BPP (130) are transmitted to the BDP (134) along the SR (132) by the LMs (110)

a set of LM guides (300) configured to maintain the LMs (110) at the essentially constant circumferential and radial position and slidable with respect to the fictive tube (180), wherein the BPP (130) and/or BDP (134) is each provided with two or more articulated LM guides (310a-c, 314a-c) of the set of LM guides, each articulated LM guide (300) in the BPP (130) and/or BDP (134) is provided with a set of discrete channels (350) each accommodating one or two LMs (110), and being open to a circumferential edge (356) of the LM guide (300), which channels are arranged around the fictive tube (180), wherein each channel is open-edged in a radial direction with respect to a circumferential edge of the body, a sheath unit (430) is disposed at least partially over each of the BPP (130) and/or BDP (134), the sheath unit (430) having less compliance in a radial direction compared with an axial direction, and comprises a first layer having little or no compliance in a radial direction, and a second layer having compliance at least in an axial direction, the first layer comprises a segmented tube (410) of a non-radially compliant material optionally heat shrink material, and the second layer comprises a compliant tube (420) and is disposed over the first layer, optionally wherein the first and second layers are not bonded together, a circumferential outer edge of the articulated LM guide (300) in the BPP (130) and/or BDP (134) is provided with a circumferential guide that defines a circumferential annular path in which a detached segment (414a) of the segmented tube (410) is retained.

A longitudinal steerable tool (100) having a proximal (20) and distal (40) end may comprise:

a set of longitudinal members, LM, (110) arranged in a longitudinal direction around a fictive tube (180) maintained at an essentially constant circumferential and radial position with respect to the fictive tube (180) and being slidable relative to the fictive tube (180), and a bendable proximal part (130, BPP), bendable distal part (134, BDP), and a shaft region, SR (132) between the BDP (134) and BPP (130) wherein movements of the BPP (130) are transmitted to the BDP (134) along the SR (132) by the LMs (110)

a set of LM guides (300) configured to maintain the LMs (110) at the essentially constant circumferential and radial position and slidable with respect to the fictive tube (180), wherein the BPP (130) and/or BDP (134) is each provided with two or more articulated LM guides (310a-c, 314a-c) of the set of LM guides, each articulated LM guide (300) in the BPP (130) and/or BDP (134) is provided with a set of discrete channels (350) each accommodating one or two LMs (110), and being open to a circumferential edge (356) of the LM guide (300), which channels are arranged around the fictive tube (180), a sheath unit (430) disposed at least partially over each of the BPP (130) and/or BDP (134), the sheath unit (430) having less compliance in a radial direction compared with in an axial direction.

The sheath unit (430) may comprise a first layer having little or no compliance in a radial direction, and a second layer having compliance at least in an axial direction.

The first layer may comprise a segmented tube (410) of a non-radially compliant material optionally heat shrink material, and the second layer may comprise a compliant tube (420) and is disposed over the first layer optionally wherein the first and second layers are not bonded together.

A circumferential outer edge of the articulated LM guide (300) in the BPP (130) and/or BDP (134) may be provided with a circumferential guide that defines a circumferential annular path into which a detached segment (410a-c) of the segmented tube (410) is retained.

The circumferential guide may be formed from discrete protrusions (364a, 364b) that project radially outwards from the circumferential outer edge (356) of the articulated LM guide (300), and is disposed at discrete positions either side of the circumferential annular path, optionally wherein discrete protrusions either side of the circumferential annular path are not aligned axially (A-A').

A detached segment (414a) of the segmented tube (410) may be made from a heat shrink polymer.

The sheath unit (430) may comprise a reinforced tubing containing a coil or braided layer and a polymeric substrate layer attached to the coil or braided layer.

The sheath unit (430) may comprise an axially compliant concertina tubing.

BRIEF DESCRIPTION OF THE FIGURES

FIG. 9A is a plan view of a channel of an LM guide of the invention together with dimensional indications, wherein the channel has a closed top edge.

FIG. 9B is a side view of a channel of an LM guide of the invention together with dimensional indications.

FIG. 10A is a plan view of a LM together with dimensional indications.

FIG. 10B is a planar section of a LM at point B in FIG. 10A together with a dimensional indications.

FIG. 11A is a plan view of a channel of an LM guide of the invention together with dimensional indications, wherein the channel has open top edge.

FIG. 11B is a side view of a channel of an LM guide of FIG. 11A together with dimensional indications.

DETAILED DESCRIPTION OF INVENTION

Figure 1:
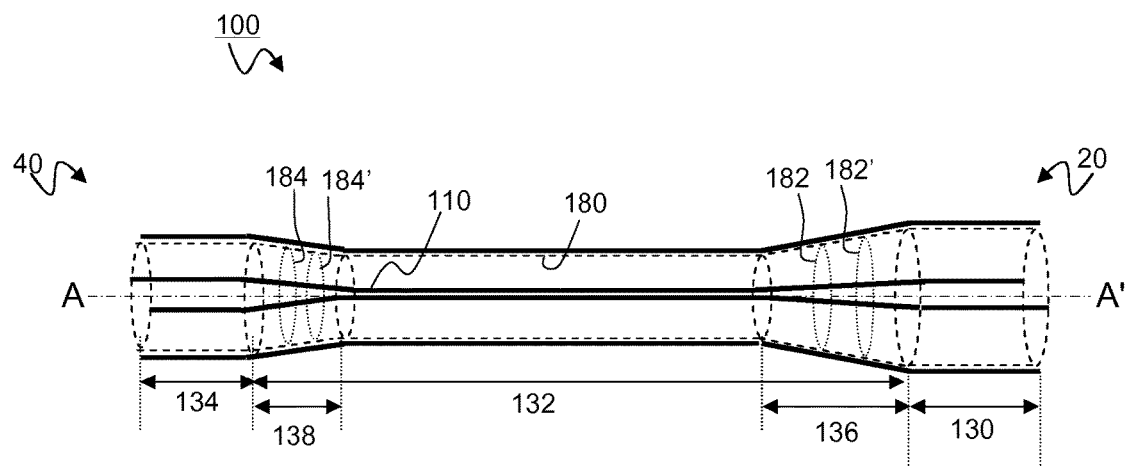
FIG. 1 is a schematic of a steerable tool described herein having a set of longitudinal members (LMs) disposed around a fictive tube provided with a proximal amplifier region (PAR) and distal attenuation region (DAR).

Before the present devices used in the invention is described, it is to be understood that this invention is not limited to particular devices described, as such devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. All publications referenced herein are incorporated by reference thereto. All United States patents and patent applications referenced herein are incorporated by reference herein in their entirety including the drawings.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The terms "distal" and "proximal" are used through the specification, and are terms generally understood in the field to mean towards (proximal) or away (distal) from the surgeon's side of the apparatus. Thus, "proximal" means towards the surgeon's side and, therefore, away from the patient's side. Conversely, "distal" means towards the patient's side and, therefore, away from the surgeon's side.

The present invention relates to a steerable tool containing a plurality of steering wires, known as longitudinal members, LM, herein which transmit movements from a bendable proximal part, BPP, along a shaft region, SR, to a bendable distal part, BDP. A movement of the BPP, transmitted via the LMs, results in a corresponding movement of the BDP. In parts or all of of the steerable tool, the LMs may be arranged around a fictive tube, for instance in the BPP and BDP, DAR or PAR where present. The LMs may be arranged around a fictive tube present at least in part of the SR (e.g. when the DAR or PAR are present). It is appreciated that for very small diameter SR or flexible SR, the LMs do not need to follow a fictive tube in the SR.

A proximal amplifier region, PAR, may be present; in the PAR the LMs are arranged around a fictive tube; the size of the fictive tube towards the distal end of the steerable tool is decreased. A proximal amplifier region, PAR, may be present in addition to a distal attenuating region, DAR; in a DAR the LMs are arranged around a fictive tube; the size of the fictive tube towards the distal end of the steerable tool is increased again. It allows the diameter of the SR to be greatly reduced, in particular allowing multiple steerable tools to enter space through a narrow opening, for instance during minimally invasive surgery. It allows multiple tools in the incision to work together, since the smaller diameter of SR allows a larger degree of freedom of movement. Further, the PAR and DAR may be configured such that there is an overall movement amplification (e.g. velocity ratio >1). For a small movement of the BPP, the operator can obtain a larger travel distance at the BDP. It finds particular utility in a surgical setting when the steerable tool is operated by digits of a single hand, and the available operating volume is limited. In a particular aspect, the LMs disposed around a fictive tube are maintained in a fixed radial position with respect to a central axis of the steerable by LM guides. The LM guide is disposed with a set of channels for holding the LMs in position. In the PAR the channels are configured to guide the LMs from a smaller fictive tube towards the distal end of the steerable tool to a larger fictive tube towards the proximal end of the steerable tool. In the DAR the channels are configured to guide the LMs from a smaller fictive tube towards the distal end of the steerable tool to a larger fictive tube towards the proximal end of the steerable tool.

The steerable tool is preferably longitudinal, meaning it is longer in one direction. It does necessarily not imply the steerable tool is linear, though a linear (straight) steerable tool is within the scope of the invention. The steerable tool may be straight or curved, for instance, having a C- or S-shape shaft region. The steerable tool may have a flexible shaft e.g. when following the blood vessels during endovascular procedures.

Typically, a steerable tool has a proximal end and distal end. The steerable tool comprises a bendable distal part that moves responsive to actuation of the steerable tool at the bendable proximal part. The BPP and BDP are sometimes known as a wrist. Actuation of the BPP induces a movement response in the BDP. The steerable tool is also provided with a shaft region, that may be flexible, at least partially flexible essentially rigid, or semi-rigid, one end of which is disposed with the BPP and the other end with the BDP. A flexible shaft region is compatible with a narrow shaft diameter as it has a negligible effect on the bending of the BDP. The shaft region, SR, is longitudinal, meaning it is longer in one direction. It does necessarily not imply the shaft region is linear, though a linear (straight) shaft is within the scope of the invention. The shaft region may be straight or curved, for instance, having a C- or S-shape. To control BPP, steering wires which are known as longitudinal members (LMs) are used. They control the BDP by pulling or pushing, hence the LM are able withstand tensile and compression forces. The steerable tool comprises a set of longitudinal members (LM) each having a proximal end and a distal end. The tip (distal terminal end) of the BDP is able to move with equal ease in any direction i.e. there is no singularity. The movement response is proportion to the degree of actuation by the BPP.

The steerable tool may contain a proximal amplifier region, PAR, and optionally a distal attenuating region, DAR. The PAR is configured to change the shape of the fictive tube such as to reduce the radial distance of the LMs with respect to a central axis of the steerable tool in the distal direction. The DAR is configured to change the shape of the fictive tube such as to increase the radial distance of the LMs with respect to a central axis of the steerable tool in the distal direction. In particular, the PAR is a region or zone in the steerable tool in which the size of the fictive tube increases from the distal end to the proximal end of the PAR. In particular, the DAR is a region or zone in the steerable tool in which the size of the fictive tube decreases from the distal end to the proximal end of the DAR. The PAR may be located in the SR and/or in the BPP. The DAR may be located in the SR and/or in the BDP. The PAR may be located at least partially, preferably fully in the BPP. The DAR may be located at least partially, preferably fully in the BDP. Preferably, the PAR is located in the SR at the proximal end. Preferably, the DAR is located in the SR at the distal end. Preferably, the PAR is located in the SR at the proximal end and contacts the BPP. Preferably, the DAR is located in the SR at the distal end and contacts the BDP.

The shaft region may be flexible, at least partially flexible, essentially rigid or semi-rigid, or may be flexible and become rigid or semi-rigid when co-operating with a rigid or semi-rigid exotube, outer tube, or inner tube. The shaft region is adjacent to the BDP. The shaft region may contact the BDP. The BPP is adjacent to the shaft region. The shaft region may contact the BPP. The SR is disposed between the BPP and BDP.

For endovascular applications or for instruments that can be used in a gastro intestinal endoscope (gastroscope or colonoscope) a flexible shaft is envisaged. A very small diameter SR is bendable; it has an advantage that bending of the harbouring shaft has no or only little influence on the bending of the BDP. In endovascular application e.g. the catheter has to make multiple bends to follow the branches of the vessels. When the diameter is so small that the LM are literally packed together, the bents of the vessels will not influence the bending of the BDP.

Movement of the BPP actuates the steerable tool at the proximal end and induces a movement response in the BDP. Movement of BPP in different radial directions and to different bending degrees is transmitted using the LMs to the BDP, and results in a corresponding change in radial direction and/or degree of bending of the BDP.

The steerable tool may be actuated at the proximal end using an electromechanical device connected directly to the MTS, for instance to two or more of the LMs, or each and every LM. Typically the LMs in the shaft region would be actuated. In such case, the tool may be devoid of a BPP. Alternatively, robotic control may be realised by using an electromechanical device to actuate the BPP. The electromechanical device may be, for instance, a servo motor. Coupling to an electromechanical device would facilitate direct integration into a surgical robot.

The steerable tool may be an engineering tool, industrial tool, or surgical instrument, having use for any type of remote robotically-controlled manipulation, sensing, or activity. The steerable tool may be a surgical instrument, such as, for instance, a minimally invasive surgical instrument, a laparoscopic instrument, an endoscopic instrument, a gastroscope, a colonoscope, ureteroscope or an endovascular catheter. The steerable tool can be used in an articulated instrument such as but not limiting to endovascular, endoscopic, neurosurgical, ENT (ear, nose and throat), orthopaedic applications, surgical instruments, robotic tele-operated medical robotics or hand-held surgical tools and industrial applications.

The steerable tool may comprise a first and second BPP tandemly arranged and that controls movement of a first and second BDP respectively tandemly arranged, as described for instance in WO 2009/098244 (see FIGS. 13A and 13B therein). In such case, a handle or connector attached to the outer most (first) BPP controls movement of the outer most (first) BDP in the same way as described herein, and is attachable to a robotic arm. The second (inner most) BPP controls movement of the second (inner most) BDP; once the desired position of second (inner most) BDP is met, the position of the second (inner most) BPP is locked using an external clamp. Alternatively, the position of second (inner most) BPP may be controlled using an index mechanism that allows selection from a plurality of fixed discrete positions.

The steerable tool may be a surgical instrument, such as, for instance, a laparoscopic instrument or an endovascular catheter. The invention can be used in an articulated instrument such as but not limiting to endovascular applications, surgical instruments, robotic tele-operated medical robotics or hand-held surgical tools and industrial applications.

The BDP is configured to move omni-directionally i.e. in any radial direction while the shaft is rotationally fixed. BDP is preferably configured to move in any radial direction (about 360° with respect to central longitudinal axis (A'-A) of the shaft part) while the shaft is axially-rotationally fixed. The BDP may be configured to bend along a curve. It might be distinguished from classical minimally invasive tools in that it may be absent of revolute joints. The movement response of the BDP may be:
  a change in degree of bending within a "bending plane" that is a plane parallel to and contacting a central longitudinal axis (A-A') of and extending from the shaft,
  a change direction of the bend; it amounts to a change in direction of the bending plane around the shaft central longitudinal axis (A-A') when the BDP lies along said bending plane.

Similarly, the BPP, is configured to move omni-directionally i.e. in any radial direction while the shaft is rotationally fixed. BPP is preferably configured to move in any radial direction (about 360° with respect to central longitudinal axis (A'-A) of the shaft part) while the shaft is axially-rotationally fixed. The BPP may configured to bend along a curve. It might be distinguished from classical minimally invasive tools in that may be absent of revolute joints. The movement response of the BPP may be:
  a change in degree of bending within a "bending plane" that is a plane parallel to and contacting a central longitudinal axis of and extending from the shaft,
  a change direction of the bend i.e. of the distal tip or end effector; it amounts to a change in direction of the bending plane around the shaft central longitudinal axis (A-A') when the BPP lies along said bending plane.

The combination of movements of the steerable tool facilitates a rotation of BPP at its tip or of the end effector while the BPP is in a bent position that is transmitted via a rotation of the shaft to the BDP that causes rotation of the BDP tip or end effector while the BDP is in a bent position. With such rotation of the tip or of the end effector, the direction of the bending plane can be maintained constant. It is appreciated that the distal tip of the BDP refers in this context to the distal terminal end of the BDP.

The combination of the movement of steerable tool further facilitates a change in direction of the BDP tip or end effector while the shaft is in a fixed rotational position. With such movement, the bending plane rotates around the shaft central longitudinal axis (A-A') while the shaft itself does not rotate.

The distal tip of the BDP may be provided with an end effector. The end effector may be rotationally fixed in relation to the BDP, and the end effector is rotatable when the BDP is in a bent position, by a complementary rotation of the BPP. The end effector may be directly attached to the distal end of the BDP (without a coupling).

The steerable tool end effector may comprise any suitable tool for a remotely controlled application, such as a screw driver, abrasive pad, drill bit, gripper, pliers, cutting scissors, camera and the like. The steerable instrument end effector may be any tool useful in a surgical procedure, tasks as gripper, pliers, cutting scissors, needle holder, retractor, camera needle, (aspiration) catheter, electrical catheter, optical (laser) fiber, ultrasound therapy, measurement probe (temperature, pH, pressure, electrophysiology), stapler, drill, electro-coagulator, HF, clip applier, fluid port and the like.

The term end effector also includes a coupling for attachment to a tool such as mentioned above. The coupling may be rotationally fixed in relation to the BDP, and the coupling is rotatable when the BDP is in a bent position, by a complementary rotation of the BPP. A tool mounted to the coupling is rotationally fixed in relation to the BDP.

The term end effector also includes a port for aspiration or passage of a second catheter such as during endovascular procedures.

Rotationally fixing the coupling or end effector relative to the BDP may be achieved using a permanent (non-adjustable) connection or joint, or by means of a lockable element configured to allow rotational adjustment of and to rotationally fix the coupling or end effector in rotational relation to the BDP.

The proximal tip of the BPP may be provided with a handle or connector or a coupling for a handle or connector. The handle, connector or coupling may be rotationally fixed in relation to the BPP. The handle or connector may be directly attached to the proximal end of the BPP (without a coupling). The coupling may be rotationally fixed in relation to the BPP. A handle or connector mounted to the coupling is rotationally fixed in relation to the BPP. Rotationally fixing the handle or connector or a coupling to the BPP may be achieved using a permanent (non-adjustable) connection or joint, or by means of a lockable element configured to allow rotational adjustment of and to rotationally fix the handle or connector or a coupling in rotational relation to the BPP. The connector allow connection of the steerable instrument to a robotic arm.

The steerable tool may contain a longitudinal sub-region that is a proximal amplifier region, PAR. The PAR is a region or zone in the steerable tool wherein the LMs are arranged around a fictive tube in which the size of the fictive tube decreases from the proximal end to the distal end of the PAR. Typically, the fictive tube leaving the PAR at its proximal end retains the larger size at least until the proximal end of the steerable tool. The PAR may be located in the SR and/or in the BPP. The PAR may be located at least partially, preferably fully in the BPP. Preferably, the PAR is located in the SR at the proximal end. Preferably, the PAR is located in the SR at the proximal end and contacts the BPP. The PAR may be located exclusively in the SR.

The PAR exhibits size-decremental fictive tube plane sections in a distal direction for at least 2 plane sections. Comparing fictive tube plane sections located at different longitudinal positions within the PAR, the plane section at the proximal side is larger than that of the distal side. When comparing sizes of a plane section, the area of the plane section outer profile is compared. A plane section is typically a transverse cross-section perpendicular to the longitudinal central (A-A') axis of the fictive tube. Where the fictive tube has a circular profile, the size of the plane section refers to its outer diameter. As a consequence of the PAR, LMs in the PAR are set at a greater radial distance from the central axis of the steerable tool, compared with the LMs in the SR.

The size of plane sections in the PAR preferably reduces gradually from the PAR proximal end to the distal end. Hence, the PAR may have the shape of a truncated cone. The size of a plane section at the distal end of the TAR may be the same as the size of a plane section in the SR. The size of a plane section at the proximal end of the PAR may be the same as the size of a plane section in the BPP.

The steerable tool may contain a longitudinal sub-region that is a distal attenuating region, DAR. The DAR is a region or zone in the steerable tool wherein the LMs are arranged around a fictive tube in which the size of the fictive tube increases from the proximal end to the distal end of the PAR. Typically, the fictive tube leaving the DAR at its distal end retains the larger size at least until the distal end of the steerable tool. The PAR may be located in the SR and/or in the BDP. The DAR may be located at least partially, preferably fully in the BDP. Preferably, the DAR is located in the SR at the distal end. Preferably, the DAR is located in the SR at the distal end and contacts the BDP. The DAR may be located exclusively in the SR.

The DAR exhibits size-incremental fictive tube plane sections in a distal direction for at least 2 plane sections. Comparing fictive tube plane sections located at different longitudinal positions within the DAR, the plane section at the proximal side is smaller than that of the distal side. When comparing sizes of a plane section, the area of the plane section outer profile is compared. A plane section is typically a transverse cross-section perpendicular to the longitudinal central (A-A') axis of the fictive tube. Where the fictive tube has a circular profile, the size of the plane section refers to its outer diameter. As a consequence of the DAR, LMs in the DAR are set at a greater radial distance from the central axis of the steerable tool, compared with the LMs in the SR.

The size of plane sections in the DAR preferably increases gradually from the DAR proximal end to the distal end. Hence, the DAR may have the shape of a truncated cone. The size of a plane section at the distal end of the DAR may be the same as the size of a plane section in the SR. The size of a plane section at the proximal end of the DAR may be the same as the size of a plane section in the BDP.

The steerable tool may both a PAR and DAR. The motion amplification (velocity or angulation ratio) caused by the PAR can be set to an over amplification. An over-amplification is a level of motion amplification that would provide insufficient force or that would cause amplify tremor movements of the hands. An over-amplification is typically a velocity or angulation ratio of greater than 2. The result of the over-amplification is a reduction in diameter of the SR, which allows the use of multiple steerable tools through the same confined opening. The DAR attenuates the amplification of the PAR, restoring forces and reducing tremor movements of the hands. An attenuating effect of a DAR typically has velocity or angulation ratio of 0.3-0.7. The combined effect of the PAR and DAR may provide a net movement amplification having a velocity or angulation ratio of 1-2.

The steerable tool comprises a set of longitudinal members (LMs) each having a proximal end and a distal end, arranged in a longitudinal direction. In parts of the steerable tool, the LMs may be arranged around a fictive tube, for instance in the BPP and BDP. The LMs may be arranged around a fictive tube present at least in part of the SR (e.g. when the DAR or PAR are present). It is appreciated that for very small diameter SR or flexible SR, the LMs do not need to follow a fictive tube. The LMs of the set contact the fictive tube. The LMs are also known as steering wires.

The distal ends of the LMs are maintained in fixed relation to each other at the distal end of the BDP. The distal ends of the LMs, more preferably the distal terminal ends of the LMs, may be connected to a distal LM fixation element. Preferably, the distal LM fixation element maintains the LMs at their respective circumferential positions, for instance, it may maintain the distal terminal ends of the LMs in an annular shape. The distal LM fixation element may be, for instance, a disc or annulus disposed at the distal end of the MTS. The distal LM fixation element is preferably rigid.

Similarly, the proximal ends of the LMs, more preferably the proximal terminal ends of the LMs, may be maintained in fixed relation to each other at the distal end of the BPP. The proximal ends of the LMs may be connected to a proximal LM fixation element. Preferably, the proximal LM fixation element maintains the LMs at their respective circumferential positions, for instance, it may maintain the proximal terminal ends of the LMs in an annular ring. The proximal LM fixation element may be a disc or annulus disposed at the proximal end of the MTS. The proximal LM fixation element is preferably rigid.

The LMs are slidable relative to each other, to the extent that movement is restricted by said LM fixation element(s). It is appreciated distal terminal ends of each LM in the set are maintained in fixed relation to each other (by the distal LM fixation elements), and the proximal terminal ends of each LM in the set are maintained in fixed relation to each other (by the proximal LM fixation elements) and hence the LMs do not slide relative to each other at the proximal and distal terminal ends. The application of force—pushing and/or pulling—at the BPP is transmitted via the LMs along the SR to the BDP which in turn causes movement of the BDP e.g. by pulling or pushing the aforementioned fixation element(s).

The number of LM in the set may be at least two, for instance, 2, 3, 4, 5, 6, 7, 8, 9, 10, 11, 12, 13, 13, 14, 15, 16, 17, 18, 19, 20, 22, 24, 26 or more. For omni-directional steering, it is preferred that at least 4, more preferably at least 6 or 8, more preferably at least 6 or 8 LMs, even more preferably 12 to 22 LMs are present in the set.

An LM has a length, thickness and width (see FIGS. 10A and 10B). A width is the distance across a plane section in longer direction. A plane section is typically a transverse cross-section perpendicular to the longitudinal central (L-L') axis of an LM. A thickness is the distance across the plane section in shorter direction. The longer and shorter directions are perpendicular to each other. Where one of the sides of the plane section is straight, one direction is parallel to said straight edge. The width of the LM may be constant in the longitudinal direction. The thickness of the LM may be constant in the longitudinal direction. The thickness and width may be the same for instance, when the planar section is square or round. The length of the LM refers to the longitudinal length.

Dimensions of an LM may depend on the diameter and length of the eventual steerable tool, and on the number of LMs utilised. As a general guidance, an LM may have a thickness in one direction of 40 µm, 50 µm, 60 µm, 80 µm, 100 µm, 200 µm, 200 µm, 400 µm or 500 µm, or a value in the range between any two of the aforementioned values. An LM may have a width of 80 µm, 100 µm, 120 µm, 140 µm, 160 µm, 180 µm, 200 µm, 300 µm, 400 µm, 500 µm, 600 µm, 700 µm, 800 µm, 900 µm, 1000 µm, 1100 µm, 1200 µm, 1300 µm, 1400 µm, or 1500 µm or a value in the range between any two of the aforementioned values. The skilled person would understand how to select a suitable thickness and width according to the SR diameter.

For a SR diameter of 3-10 mm, the preferred thickness is 70 µm to 400 µm, preferably about 300 µm, and the preferred width is 120 µm to 600 µm, preferably about width 500 µm. The length of the MTS will depend on the length of the steerable tool and its application. The above preferred dimensions apply to MTS of 37-40 cm in length.

The LMs may be made from any suitable material having the appropriate tensile and compression properties and can be deduced by the person skilled in the art. Preferably the LMs are made from a non-compressible material. Examples include stainless steel or nitinol, beta titanium, spring steel, or polymer.

The LM may be made from a single strand of a material e.g. a single strip of stainless steel. Alternatively, it may be made from multiple strands of material tandemly connected.

The LMs are longitudinally arranged around the fictive tube. The LMs may be distributed evenly around the fictive tube e.g. the distance between adjacent LMs may be essentially the same. The LMs may distributed symmetrically around the fictive tube e.g. there may be a plane of symmetry about a longitudinal-cross section of the fictive tube. The LMs may be distributed unevenly around the fictive tube e.g. the distance between at least two pairs of adjacent LMs may be different.

The LM is preferably disposed essentially along the length of the steerable tool. It spans the BDP and extends into the SR, and the BPP where present. The LMs are preferably arranged such that their longitudinal axes are mutually parallel. The LMs are preferably arranged such that their longitudinal axes are parallel to a longitudinal axis (A-A') of the fictive tube. The LMs are preferably arranged such that their longitudinal axes are parallel to a longitudinal axis of the longitudinal steerable tool. The LMs may be arranged such that their longitudinal axes form a spiral.

In parts or all of the steerable tool, the LMs may be arranged around a fictive tube, for instance in the BPP, BDP, PAR, and/or DAR. The LMs may be arranged around a fictive tube present at least in part of the SR (e.g. when the DAR or PAR are present), or all of the SR. It is appreciated that for very small diameter SR or flexible SR, the LMs do not need to follow a fictive tube. A fictive tube has a proximal and a distal end, which corresponds to the proximal and distal ends of the steerable tool. A fictive tube has a central axis corresponding to the central axis (A-A') of the steerable tool.

The fictive tube is preferably longitudinal. It preferably has a circular plane section, a plane section being essentially perpendicular to a longitudinal axis and referring to the outer profile. Other plane sections are envisaged, however, such as oval. Preferably the shape of the plane section, e.g. circular or oval, is the same throughout the fictive tube, though transitioning, preferably gradual transitioning, between one or more shapes is within the scope of the invention. A central axis (A'-A) of the fictive tube is preferably coaxial with a central axis of the steerable tool. The fictive tube is preferably cylindrical. The fictive tube has diameter that is smaller than the diameter of the steerable tool at the corresponding position. The LMs follow the longitudinal shape of the fictive tube. Where the fictive tube contains the proximal amplifier region, PAR, for instance, the LMs follow the reduction in distance from the central axis in the distal direction. Where the fictive tube contains the distal attenuation region, DAR, for instance, the LMs follow the increase in distance from the central axis in the distal direction.

The LMs may be maintained in radial and circumferential alignment around the fictive tube using a set of LM guides. The steerable tube may be provided with a set of LM guides configured to support and maintain the arrangement of LMs around the fictive tube. There may be 2 to 30, more preferably 3 to 20 LM guides in the set. The set of LM guides maintain the set of LMs at a constant circumferential position on the fictive tube, and slidable relative thereto. It is appreciated that at gaps between LM guides, the circumferential position of the LMs may change relative to the fictive tube. In particular, the set of LM guides may axially rotationally constrain the LMs of the set, in particular at the BDP and BPP.

One or more LM guides of the set ("articulated LM guides" herein) may be articulated with respect to each other, particularly mutually pivoted, thereby supporting bending of the LMs, akin to a wrist joint. Articulated LM guides may be disposed in the BDP and in the BPP. In a steerable tool of 30 to 40 cm in length and a diameter of 6 mm to 8 mm, the BDP may contain between 3 and 10 articulated LM guides. The distance between adjacent articulated LM guides may not exceed 12 mm, more preferably 10 mm when the LM guides are aligned in a straight line. This is to avoid buckling of the LMs.

One or more LM guides of the set ("fixed LM guides" herein) may be rotationally fixed with respect to each other, thereby maintaining a fixed (non-bending) path of the LM. Fixed LM guides may be disposed in the SR of the steerable tool, giving rise to an essentially rigid or semi-rigid SR. In a steerable tool of 30 to 40 cm in length and a diameter of 6 mm to 8 mm, the SR may contain 1 continuous LM guide, 2 or more LM guides, preferably between between 13 and 17 fixed LM guides. There may no LM guides in the SR of the steerable tool allowing the LMs to slide directly past each other, or within a flexible guide. The positions of the LMs would be restored by LM guides in BDP and BPP.

The PAR may comprise at least two LM guides of the set. Each LM guide may provide a discrete point of contact with each LM. For instance, in FIG. 5, the PAR (136) comprises a plurality of LM guides (316a-c) each providing a discreet discrete point of contact with each LM in a longitudinal direction. Each LM guide is individual.

Figure 21:
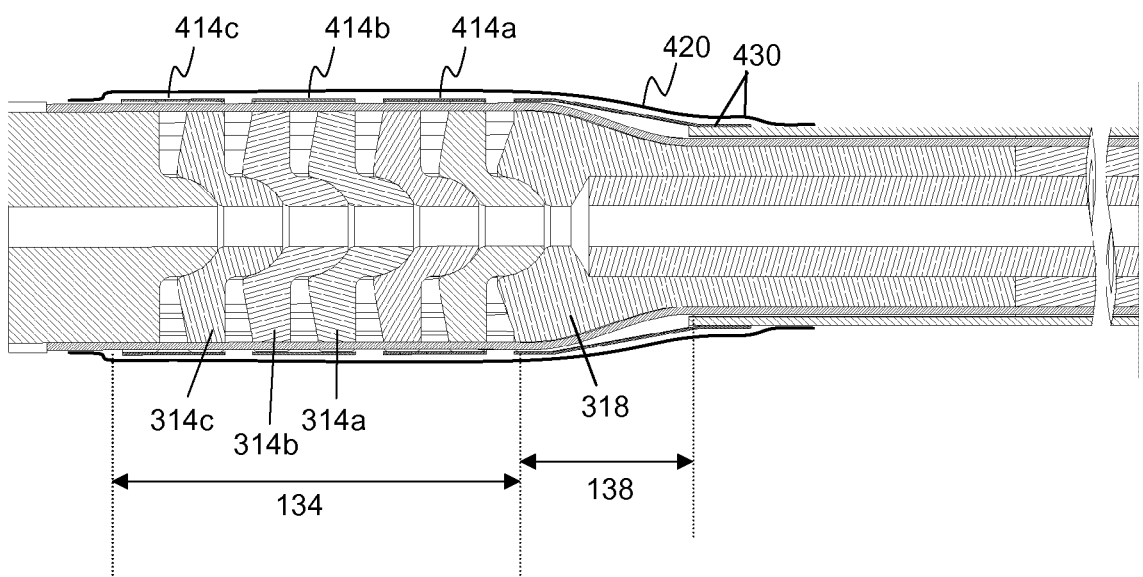
FIG. 21 shows a cross-sectional view of a BDP and DAR, wherein the DAR is formed from a single LM guide having a continuous channel.

The DAR may comprise one or at least two LM guides of the set. Each LM guide may provide a discrete point of contact with each LM. For instance, in FIG. 6, the DAR (138) comprises a plurality of LM guides (318a-c) each providing a discreet discrete point of contact with each LM in a longitudinal direction. Each LM guide is individual. In FIG. 21, the DAR (238) is formed from a single LM guide.

Where a PAR or DAR is disposed in the SR, the PAR or DAR may contain one or a plurality of fixed LM guides giving rise to an essentially rigid or semi-rigid PAR or DAR. According to one aspect, the arrangement of LMs in the PAR or DAR is realised by one or more fixed LM guides that across the length of the PAR or DAR bring the radial position of the LMs closer to the central axis of the MTS in the distal direction (PAR) or proximal direction (DAR). In other words, the channels of consecutive fixed LM guides in the PAR decrease incrementally in distance from the central axis of the MTS in the distal direction, or the channels of consecutive fixed LM guides in the DAR increase incrementally in distance from the central axis of the MTS in the distal direction. The fixed LM guides disposed in the PAR may constitute an overall truncated conical shape. The wider end of the cone is orientated in the proximal direction. The fixed LM guide or guides disposed in the DAR may constitute an overall truncated conical shape. The wider end of the cone is orientated in the distal direction. According to one aspect, the DAR comprises at least two inter-engaging parts that cooperate to form closed channels that guide each of the LM from the first radial distance to the second radial distance.

Where the PAR is disposed in the BPP, the PAR will contain the articulated LM guides giving rise to an articulated PAR and hence articulated BPP. According to one aspect, at least two LM guides in the set disposed in the PAR are articulated LM guides tandemly arranged in the PAR, each articulated with respect to an adjacent articulated LM guide, thereby supporting bending of the LMs in the PAR. The one or more, preferably at least 2 articulated LM guides in the BPP across the length of the PAR bring the radial position of the LMs closer to the central axis of the MTS in the distal direction. In other words, the channels of consecutive articulated LM guides in the PAR (and hence in the BPP) incrementally decrease in distance from the central axis of the tool in the distal direction. The articulated LM guides disposed in the PAR (and hence in the BPP) may constitute an overall truncated conical shape. The wider end of the cone is orientated in the proximal direction.

Where the DAR is disposed in the BDP, the DAR will contain the articulated LM guides giving rise to an articulated DAR and hence articulated BPP. According to one aspect, at least two LM guides in the set disposed in the PAR are articulated LM guides tandemly arranged in the DAR, each articulated with respect to an adjacent articulated LM guide, thereby supporting bending of the LMs in the DAR. The one or more, preferably at least 2 articulated LM guides in the BDP across the length of the DAR bring the radial position of the LMs closer to the central axis of the MTS in the proximal direction. In other words, the channels of consecutive articulated LM guides in the DAR (and hence in the BDP) incrementally increase in distance from the central axis of the tool in the distal direction. The articulated LM guides disposed in the DAR (and hence in the BDP) may constitute an overall truncated conical shape. The wider end of the cone is orientated in the distal direction.

An LM guide comprises a body having a distal side and a proximal side, and an outer edge or surface connecting the distal and proximal sides.

Figure 7:
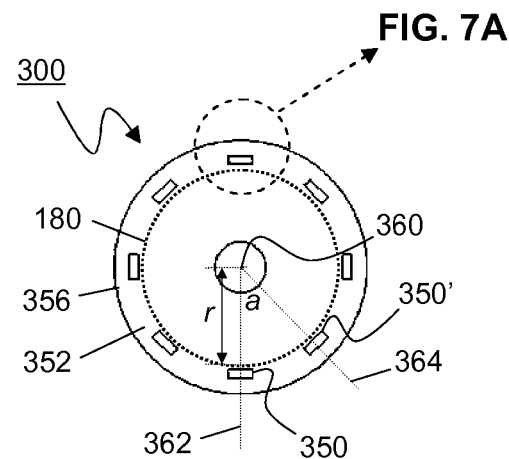
FIG. 7 is a plan view of an LM guide provided with a set of channels arranged around the fictive tube.
Figure 7A:
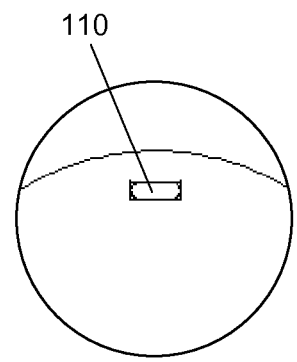
FIG. 7A is a detailed view of a channel of FIG. 7 into which a LM is disposed.
Figure 8:
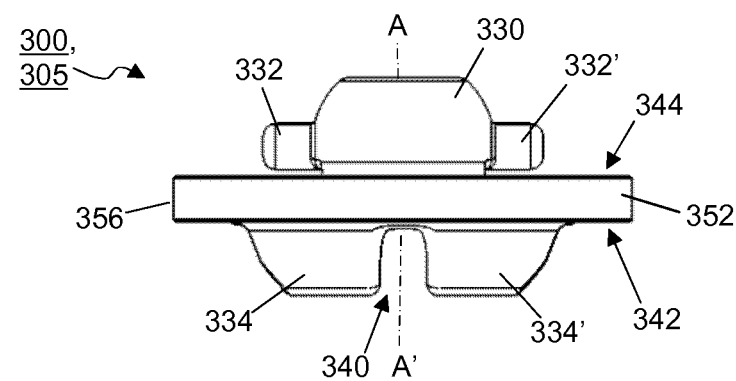
FIG. 8 is a side view of an articulated LM guide.

For an articulated LM guide, the body is preferable substantially disc-shaped as shown, for instance, in FIGS. 7, 7A and 8. The body may be disposed with one component of a pair of components of a pivot joint on the proximal side of the body and the other component of the pair on the distal side of the body. Such a pivot joint may be a ball and socket joint. Alternatively, articulated LM guides by articulated by a solid member joined to one of the pair of articulating LM guides. Alternatively, articulated LM guides may be joined using a flexible material such as rubber or silicone. Adjacent articulated LM guides hence form a joint for mutual pivoting.

Where the PAR and TAR are present, largest disc-shaped body present in the BPP typically has a larger diameter compared with the largest disc-shaped body present in the BDP, for instance, 10%, 20%, 40%, 60%, 80%, 100%, 150%, 200%, 250%, 300%, 350%, or 400% larger, or value in the range between any two of the aforementioned values.

Where the PAR is present in the BPP, the BPP may comprise a plurality of articulated LM guides having a disc-shaped bodes having respective diameters decreasing gradually or stepwise from the proximal to the distal direction. The decrease may be 0.1, 0.2, 0.3, 0.4, 0.5, 0.6 cm per 1 cm of longitudinal distance in the PAR.

Where the DAR is present in the BDP, the BDP may comprise a plurality of articulated LM guides having a disc-shaped bodes having respective diameters increasing gradually or stepwise from the proximal to the distal direction. The decrease may be 0.1, 0.2, 0.3, 0.4, 0.5, 0.6 cm per 1 cm of longitudinal distance in the PAR.

Figure 5:
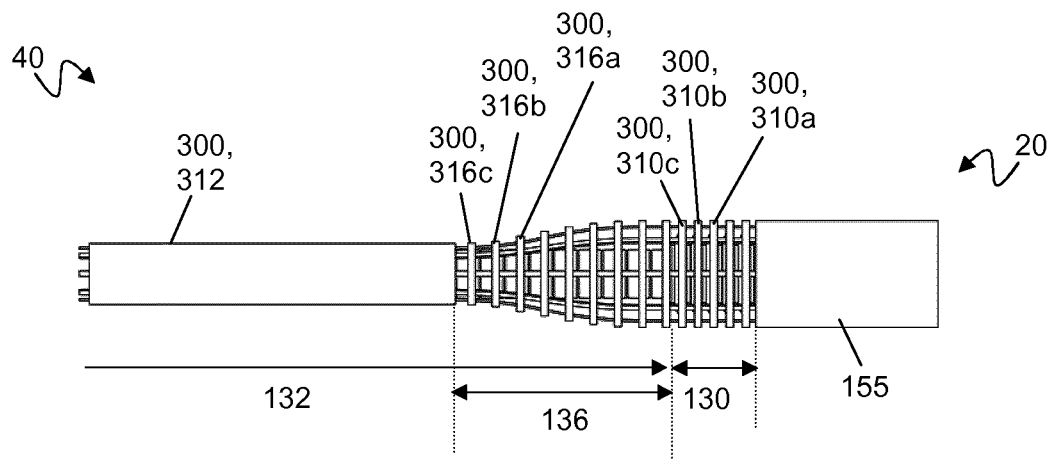
FIG. 5 is a plan view of the proximal end of a steerable tool provided with a PAR.
Figure 6:
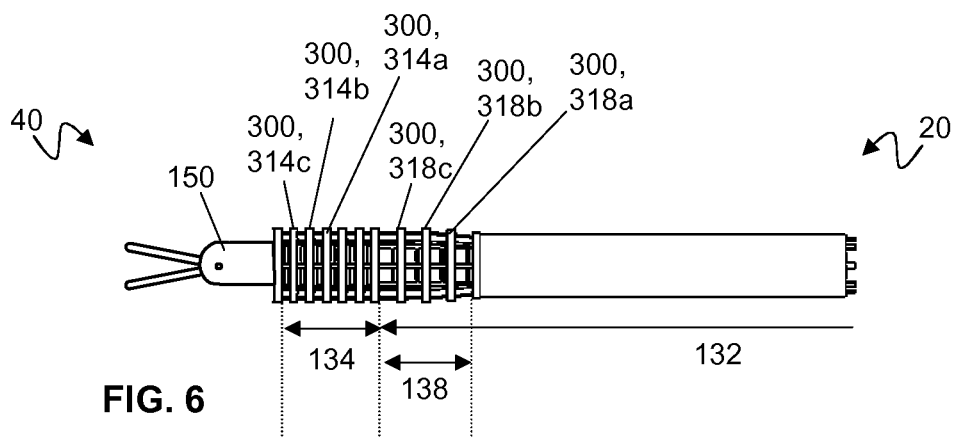
FIG. 6 is a plan view of the distal end of a steerable tool provided with a DAR.

For a fixed LM guide, preferably one located in the SR, the body may be substantially cylindrically shaped, the ends of the cylinder being the distal and proximal sides. While it is preferred that a plurality of tandemly arranged, fixed LM guides is present, it is within the scope of the invention that a single continuous fixed LM guide is disposed in the SR, corresponding to the SR of the steerable tool; such embodiment may apply when a PAR is present in the BPP and a DAR is in the BDP. A single continuous fixed LM guide may be formed by known processes such as extrusion. By tandemly arranged it is meant that the fixed LM guides are arranged end to end. Specifically, the proximal side of one fixed LM guide is in contact with the distal side of an adjacent fixed LM guide within the tandem arrangement. It is within the scope of the invention that there is one fixed LM guide.

Where a PAR or DAR is present in the SR, the body of the fixed LM guide in the PAR or DRA is preferable substantially disc-shaped as shown, for instance, in FIGS. 5 and 6. Such PAR or DAR may contain a plurality of fixed LM guides, preferably more than 3, 5, or 7, more preferably between 5 and 10. The body may be disposed with one component of a pair of components of a spacing joint on the proximal side of the body and the other component of the pair on the distal side of the body. A one component of a spacing joint is typically a protrusion (e.g. cylindrical protrusion) that provides a fixed distance between the adjacent fixed LM guide, and the other component is typically a reciprocating slot (e.g. cylindrical slot) for aligning the protrusion of an adjacent fixed LM guide. The spacing joint is fixed i.e. non-rotating and non-displacing. The spacing joint is preferably centred on the central axis of the MTS. The plane section of the spacing joint is preferably smaller than the plane section of the fictive tube. The spacing joint may be fixed using an adhesive.

Where the PAR is present in the SR, the PAR may comprise a plurality of fixed LM guides having a disc-shaped bodes having respective diameters decreasing gradually or stepwise from the proximal to the distal direction. The decrease may be 0.1, 0.2, 0.3, 0.4, 0.5, 0.6 cm per 1 cm of longitudinal distance in the PAR.

Where the DAR is present in the SR, the DAR may comprise a plurality of fixed LM guides having a disc-shaped bodes having respective diameters increasing gradually or stepwise from the proximal to the distal direction. The increasing may be 0.1, 0.2, 0.3, 0.4, 0.5, 0.6 cm per 1 cm of longitudinal distance in the DAR.

The body of the LM guide, either articulated or fixed may be a one-piece element, e.g. is formed by moulding, extrusion or machining as one piece, avoiding the assembly of a plurality of elements. The body of the LM guide is also known as an integer part. The use of a one piece element eliminates the presence of crevices or air gaps around corners of the channels, through which an LM might pass and become lodged.

In particular construction (e.g. by injection moulding) of a single continuous solid body incorporating the channels that taper so as to change their radial distance would problematic. It would require the use of a plurality of cores, one for each channel, that are positioned at an angle. Withdrawing the cores at the same time as the mould is linearly separated would cause damage to the channels. Moulding would require the angular removal of the cores that is distinct from the linear separation of the mould elements i.e. a two-step process.

The body of the LM guide is provided with a set of channels. The number of channels in the set may be at least two, for instance, 2, 3, 4, 5, 6, 7, 8, 9, 10, 11, 12, 13, 13, 14, 15, 16, 17, 18, 19, or 20, or more. For omni-directional steering, it is preferred that at least 4, more preferably at least 6 or 8 channels are present in the set. The number of channel in the set of channels may be equal to the number of LMs in the set of LMs. A channel comprises a void space in the body of LM guide. A channel passes from the distal side to the proximal side of the LM guide body. A channel connects the distal side to the proximal side of the LM guide body. A channel preferably has a central axis from the distal side to the proximal side of the body that is parallel to the central axis (A-A') of the LM guide. Each and every channel of the set may be separate; in other words, the channels may not be interconnected. A channel can accommodate one, two, or more LMs, preferably only one LM. A channel is configured to constrain the LM, in particular to prevent radial movement with respect to the central axis of the body. A channel may be configured to constrain the LM, to prevent axial rotation, i.e. about the LM longitudinal (L-L') axis. A channel is dimensioned to facilitate longitudinal slidable movement of the LM therethrough. A channel may be closed or open with respect to a circumferential edge of the body. A channel may be formed from a single element. A channel provides a discrete point of contact for the LM. The channels are arranged around and contact the fictive tube as described elsewhere. The channels of the set are mutually spatially separated. A channel may contain a transverse profile that complements the profile of the LM to be accommodated. A transverse profile is perpendicular to the central axis of the channel. For instance, where the LM has a rectangular profile, the channel may contain a rectangular profile. It is appreciated that the channel profile need not precisely mirror the profile of the LM, for instance a race-track LM profile may be constrained by a rectangular channel.

A channel has a width (320), height (322) and thickness (328) (see FIGS. 9A, 9B, 11A, 11B). The thickness is equal to the thickness or width of the body of the LM guide. The height of the channel is the smallest distance from a base wall of the channel to a top wall (FIG. 9A) or circumferential edge (FIG. 11A) of the channel measured in a straight line on a plane section of the channel perpendicular to the central axis. The width of the channel is the smallest distance between opposing channel side walls measured in a straight line on a plane section of the channel perpendicular to the central axis. The base wall, top wall and side walls are preferably planar.

For LM guides present in the PAR or DAR, the set of channels present in each LM guide may be adapted to guide the LM along an incline. When the channel thickness is too great, or the channel height is too small, the LM is restricted in its passage. One adaptation is to reduce the channel thickness; each channel may have a central axis from the distal side to the proximal side of the body that is parallel to the central axis (A-A') of the LM guide. Another adaptation is to change the geometry of the channel, for instance to introduce an inclination; each channel in the PAR or DAR may have a central axis from the distal side to the proximal side of the body that is inclined to the central axis (A-A') of the LM guide. This might be achieved using, for instance, a wedge-shaped channel that has a reduced height on one side (e.g. on the distal side) of the LM guide that increases in the proximal direction towards a higher channel opening on the other side (e.g. on the proximal side) of the LM guide (that is compatible with a molding process). Alternatively the height of channel may be equally increased through the thickness of the LM guide which would accommodate an incline of the inserted LM. Alternatively the channel may have a concave shape, which would accommodate an incline of the inserted LM (see FIG. 20). The skilled person would understand how to determine the shape of the channel from the channel thickness, and the incline of the LM that must be accommodated.

The set of LM guides are tandemly arranged i.e. distal side of one LM guide faces the proximal side of an adjacent LM guide. An example of tandemly-arranged articulated LM guides is shown in FIGS. 2, 3, 5 and 6. The articulated LM guides in the set of LM guides are mutually (pairwise) articulated. Preferably, the articulated LM guides are in mutual (pairwise) contact. Preferably, an articulated LM guide contacts an adjacent LM guide using a pivot joint, such as a ball-and-socket type joint. The pivot joint allows pivoting of an articulated LM guide with respect to an adjacent articulated LM guide. The pivot joint may allow two degrees of freedom of movement with respect to an adjacent articulated LM guide i.e. roll and pitch. The pivot joint may or may not also allow relative rotation of adjacent articulated LM guides (i.e. yawing or axial rotation between adjacent articulated LM guides). Prevention of yawing can be achieved for instance, using a rotation limiter that might be a protrusion fixed on the body of one articulated LM guide that is received by a recess fixed on the body of an adjacent articulated LM guide (as shown, for instance, in FIG. 8); coupling prevents axial rotation of one LM guide relative to the adjacent LM guide.

The one or more fixed LM guides of the set of LM guides are mutually (pairwise) in fixed relation. They are preferably in fixed rotational relation. They are preferably in fixed distance relation. Preferably, the one or more fixed LM guides are in mutual (pairwise) contact.

The LM guides of the set are tandemly arranged such the circularly-arranged channels are in alignment, and each can receive one (or optionally two or more) LMs.

Each channel is configured to constrain the LM to reduce or prevent axial rotation, and to maintain its radial position with respect to a central LM guide axis (A-A').

A channel of an LM guide may be open-edged, meaning that the channel in a radial direction is open with respect to a circumferential edge of the body, as shown, for instance, in FIG. 11A. The channel width (FIG. 11A, 320) may be equal to or greater than an LM width (FIG. 10A, 124). To retain the LMs within the channels, a sheath unit is disposed at least partially over the open-edged LM guides.

The sheath unit has less compliance in a radial direction compare with in an axial direction. The sheath unit may have little- or no-compliance in a radial direction, and compliance in axial direction. The sheath unit may be axially flexible.

By compliance it is meant elasticity; the ability to expand or compress upon application of an external force, and return to an initial form when the external force is removed. A radial direction refers to a radial direction from a central (A-A') axis of the steerable tool, and an axial direction refers to direction parallel to or along central (A-A') axis of the steerable tool in a straight or bent position.

The sheath unit may be applied at least partially over the BPP and/or over the BDP. The sheath unit may be applied over the BPP and/or over the BDP. The sheath unit may be applied at least over the BPP and/or over the BDP. The sheath unit may be applied only over the BPP and/or over the BDP.

The non- or reduced-radial compliance of sheath unit retains the LM within the channels in the BPP or BDP during bending, while the axial compliance allows to stretch over the longer (outer) curve and fold or crumple with respect to the shorter (inner) curve during bending.

The properties of the sheath unit may be realised by a combination of different layers.

The sheath unit may comprise a first layer having little or no compliance in a radial direction, and a second layer having compliance at least in an axial direction. The first layer maybe flexible. The second layer may be flexible.

The first layer may be a segmented tube of a non-compliant material. The non-compliant material may be a heat-shrink polymer. A heat shrink polymer may be applied over one or a plurality of open-edged LM guide while in a non-shrink state, and the application of heat brings the segmented tube into contact with the open-edged LM guide or guides and/or LMs thereon. In the heat-shrink state, the segmented tube may apply inner radial forces i.e. towards a central (A-A') axis. At least one, preferably all of the segments in the segmented tube may be detached from any adjacent segment(s). The detached segments may slide relative to each other during bending of the BPP or BDP. At least one, preferably all of the segments in the segmented tube may be connected by a joint that does not block bending of the BDP or BPP. The detached segments may deform e.g. crumple during bending of the BPP or BDP; this allows bending of the BPP or BDP without blocking.

The segments of the segmented tube may be arranged so as to cover at least a part of a LM guide and/or the LMs thereon. Advantageously, there is no requirement that they are located within the gaps between the LM guides which would require certain manufacturing tolerances, and would block the bending of the BPP and BDP.

The sum of the widths of the segments may be between 25% or 100% of the length of inner arc length in full bent position. If less than 25% the LMs may have a tendency to lift from the open channels. When more than 100% the segments may collide with each other and inhibit bending.

According to one aspect, a circumferential outer edge of the LM guide is provided with a circumferential guide that defines a circumferential annular path into which the segments of the segmented tube can locate and be retained. The circumferential guide retains the tube segment on the LM guide, and the tube segment retains the LMs within the channels. The circumferential guide is preferably formed from discrete protrusions that project radially outwards from the circumferential outer edge of the LM guide, and are disposed at discrete positions either side of the circumferential annular path. It is preferred that the discrete protrusions either side of the circumferential annular path are not aligned axially (A-A'); this allow the LM guide to be formed in a two-piece mould; undercuts are avoided.

The second layer may be compliant tube that is compliant in at least an axial direction and optionally in a radial direction. The compliant tube covers the segmented tube. It may or may not be bonded to the first layer. The compliant tube may apply an inward radial force to the segmented tube which maintains the segments in approximately similar axial position. The second layer assists in maintaining the position of the segments so that they remain distributed along the BPP or BDP after repeated bending.

The sheath unit may comprise a reinforced tubing containing a coil or braided layer, and a substrate layer. The common braid/coil material may be made from nitinol or steel. It may have a round or flat cross-sectional profile. With respect to a braided layer the axial compliance is determined by the per inch crosses (PIC count), whereby axial compliance (and flexibility) increases with increasing PIC count. The substrate layer may contain polyimide, PTFE liners and a thermoplastic material such as like pebax or nylon. The substrate layer is bonded by melting with respect to the coil or braided layer. An interior and or exterior surface of the reinforced tubing made by provided with a layer to reduce friction such as PTFE. An exterior made be provided with a layer to increase durability such as polyimide, pebax, nylon and a urethane. Examples of a suitable reinforced tubing are those manufactured by MicroLumen (US)

The sheath unit may comprise a concertina tubing. A concertina tubing has a longitudinal expanded state and a folded state. It is corrugated in a longitudinal direction. By application of axial tension the concertina tubing transitions to the expanded state. Because of the compliance in the axial direction, the concertina tubing transitions to the folded state upon release of the axial tension.

Where the DAR or PAR is formed from a plurality of separate LM guides that have a disc-shaped body, and a spacing joint separating the disc-shaped body, a channel of such LM guide may be open-edged, meaning that the channel in a radial direction is open with respect to a circumferential edge of the body. The channel width maybe equal to or greater than an LM width. To retain the LMs within the channels, a ring of flexible or foldable, non-radially compliant material made be disposed in spaces separating the disc-shaped bodies. A radial direction refers to a radial direction from a central (A-A') axis of the steerable tool.

The ring may be made from a heat-shrink polymer. The heat shrink polymer may be applied over the space between the LM guides while in a non-shrink state, and the application of heat brings the into contact with the LMs bridging the open-edged LM guide or guides. In the heat-shrink state, the ring may apply inner radial forces i.e. towards a central (A-A') axis. The flexible or foldable property of the ring material allows it to deform e.g. crumple during bending of the BPP or BDP; this allows bending of the BPP or BDP without blocking.

Where the DAR or PAR is formed from a plurality of separate LM guides that have a disc-shaped body, and a spacing joint separating the disc-shaped body a channel of such LM guide may be open-edged, meaning that the channel in a radial direction is open with respect to a circumferential edge of the body. A radial direction refers to a radial direction from a central (A-A') axis of the steerable tool. The channel width maybe equal to or greater than an LM guide width (328). To retain the LMs within the channels, an LM guide may be disposed with a circumferential guide (e.g. FIG. 19) that retains a detached segment (414*a*) of the segmented tube (410) over a circumferential edge of the LM guide (300), preferably within a width (328) of the LM guide (300).

The circumferential guide may be formed from discrete protrusions (364*a, b*) that project radially outwards from the circumferential outer edge (356) of the LM guide (305), and are disposed at discrete positions either side of the circumferential annular path. The discrete protrusions (364*a, b*) are not aligned axially at the same radial position. Each protrusion (e.g. 364*a*) aligns axially with the circumferential outer edge 356 (e.g. 362*a*) that is not disposed with a protrusion. The protrusions act as stop members, retaining the segment (414*a*) of the segmented tube (410) around the periphery of the LM guide (300). The arrangement of non-axially aligning protrusions allows ease of manufacture in a two-piece mould; undercuts are avoided.

Reference is made in the description below to the drawings which exemplify particular embodiments of the invention; they are not at all intended to be limiting. It will be understood that the skilled person may adapt the device and substitute components and features according to the common practices of the skilled artisan.

FIG. 1 is a schematic of steerable tool 100 having a proximal 20 and distal end 40, and a central longitudinal axis A-A'. The steerable tool 100 contains a bendable distal part (BDP) 134, a shaft region (SR) 132, and a bendable proximal part 130 (BPP) tandemly arranged from the distal end 40 to the proximal end 20. A proximal amplifier region (PAR) 136 is provided in the SR 132. A distal attenuation region (DAR) 138 is provided in the SR 132. Longitudinal members, LMs 110 are arranged around a fictive tube 180 having a central longitudinal axis (A-A') that is the same as the central longitudinal axis of the steerable tube 100. The LMs 110 are maintained at essentially constant radial and circumferential position relative to the fictive tube 180. The LMs 110 are slidable relative to the fictive tube 180. In the PAR 136 the relative sizes of plane sections 182, 182' decreases in a distal 40 direction. In the DAR 138 the relative size of plane sections 184, 184' increases in a distal 40 direction. The PAR 136 and DAR 138 each has a truncated conical appearance; for the PAR 136 the base of the cone points in the proximal 20 direction. For the DAR 138 the base of the cone points in the distal 40 direction.

Figure 2:
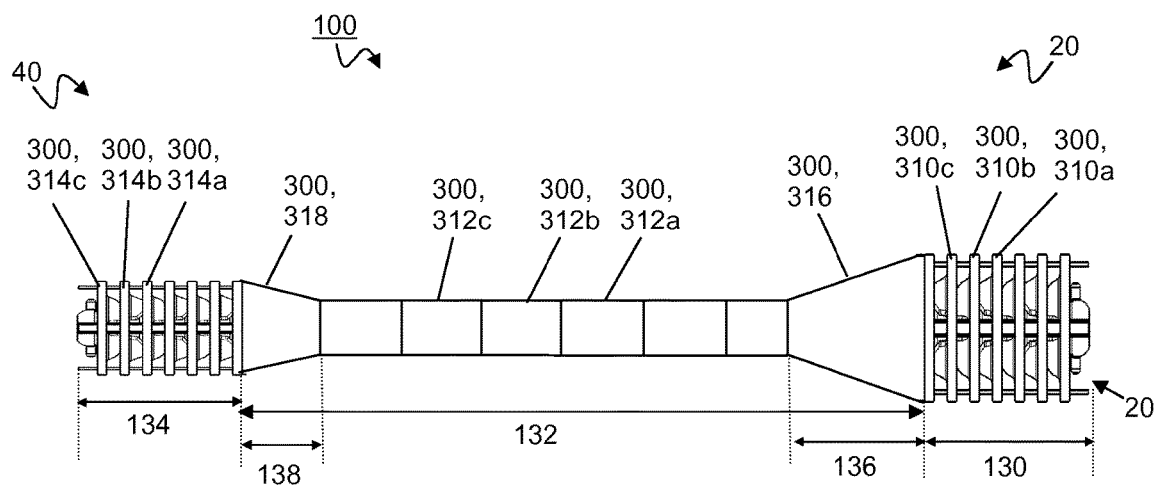
FIG. 2 depicts a plan view of a steerable tool described herein provided a proximal amplifier region (PAR) and distal attenuation region (DAR) whereby radial and circumferential position of the longitudinal member are maintained around the fictive tube by longitudinal member (LM) guides

FIG. 2 depicts a plan view of steerable tool 100 having a proximal 20 and distal end 40, and bendable distal part (BDP) 130, a shaft region (SR) 132, and a bendable proximal part (BPP) 134 tandemly arranged from the distal end 40 to the proximal end 20. A proximal amplifier region (PAR) 136 is provided in the SR 132. A distal attenuation region (DAR) 138 is provided in the SR 132. A set of LM guides 300 is indicated. The shaft region (SR) 132 is disposed with a plurality of fixed LM guides 312a-c. The PAR 136 is provided with a plurality (not shown) of fixed LM guides 316. The DAR 138 is provided with a plurality (not shown) of fixed LM guides 318. The BPP 130 is disposed with a plurality of articulated LM guides 310a-c. The BDP 130 is disposed with a plurality of articulated LM guides 314a-c. The LM guides maintain the LMs 110 at essentially constant radial and circumferential position relative to the fictive tube. The LMs 110 are slidable relative to the LMs guides 300.

Figure 3:
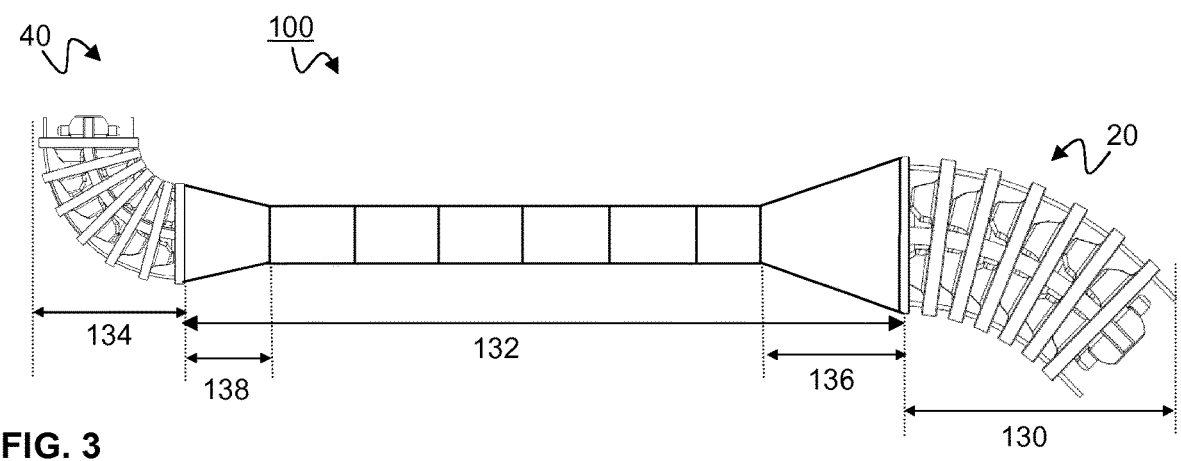
FIG. 3 depicts an actuated steerable tool of FIG. 2.

FIG. 3 depicts the steerable tool 100 of FIG. 2, in which BPP 130 has been actuated by bending, the movement transmitted to the BDP 134 along the SR 132 by the LMs, which BDP 134 bends responsively.

Figure 4:
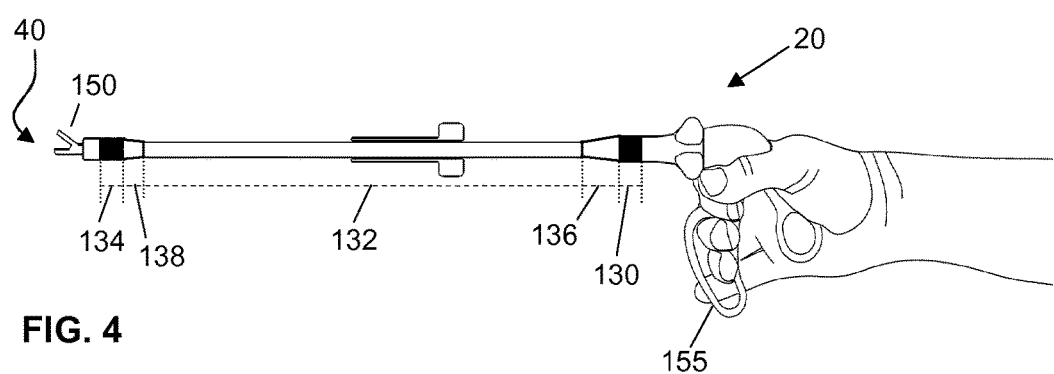
FIG. 4 depicts an isometric view of a steerable tool with an end effector and handle, and provided with a PAR and DAR.

FIG. 4 is an isometric view of a steerable tool 100 incorporating the PAR 136 and DAR 138. The steerable tool 100 has a proximal 20 and distal 40 end. The distal end 40 is provided with an end effector 150 that is a gripper, while the proximal end 20 is provided with a handle 155 to steer the tube and to control the gripper. Also indicated are the bendable distal part (BDP) 134, the shaft region (SR) 132, the bendable proximal part (BPP) 136, and the PAR 136 and DAR 138 in the SR 132.

FIG. 5 is a plan view of the proximal end 20 of an steerable tool 100. The shaft region (SR) 132 is disposed with a single fixed LM guide 312. The PAR 136, in the SR 132 is disposed with a plurality of fixed LM guides 316a-c. These are spatially fixed relative to the fixed LM guide of the SR and also with respect to each other. The BPP 130 is disposed with a plurality of articulated LM guides 310a-c. The proximal end 20 of the BPP 134 is provided with a handle 155.

FIG. 6 is a plan view of the distal end 40 of an steerable tool 100. The shaft region (SR) 132 is shown. The DAR 138, in the SR 132 is disposed with a plurality of fixed LM guides 318a-c. These are spatially fixed relative to the fixed LM guide of the SR and also with respect to each other. The BDP 134 is disposed with a plurality of articulated LM guides 314a-c. The distal end 40 of the BDP 134 is provided with an end effector 540.

Figure 6A:
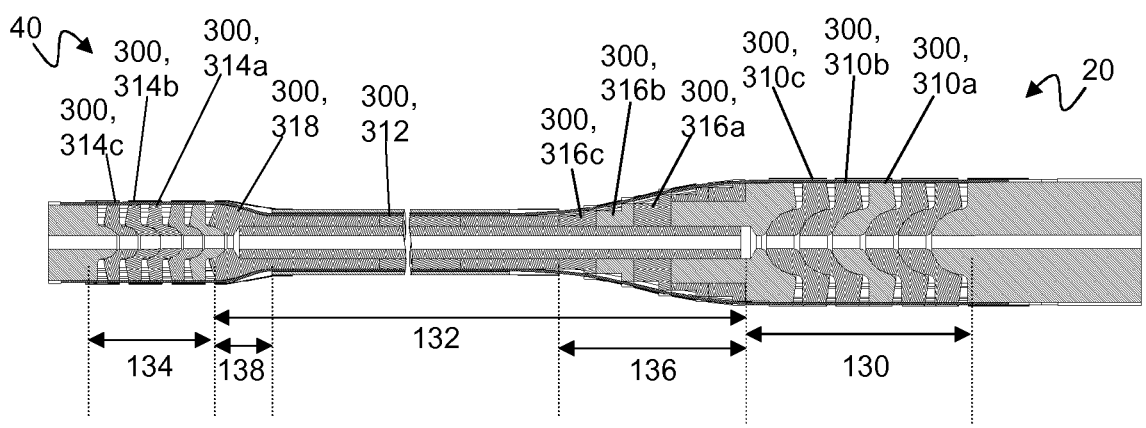
FIG. 6A is a cross-sectional view of a steerable tool provided with a PAR and DAR.

FIG. 6A is a cross-sectional view of the steerable tool 100 provided with a PAR 136 and DAR 138. The shaft region (SR) 132 is disposed with a single fixed LM guide 312. The PAR 136, in the SR 132 is disposed with a plurality of fixed LM guides 316a-c. These are spatially fixed relative to the fixed LM guide of the SR and also with respect to each other. The BPP 130 is disposed with a plurality of articulated LM guides 310a-c. The proximal end 20 of the BPP 134 is provided with a handle 155. The DAR 138, in the SR 132 is disposed with a single fixed LM guide 318. The BDP 134 is disposed with a plurality of articulated LM guides 314a-c.

FIG. 7 is a plan view of an LM guide 300 provided with a set of channels 350, 350' in the body 352 arranged around a fictive tube 180. Each channel 510 is in a fixed position relative to a central axis 360 of the fictive tube 180 or LM guide 300. As such the channel 510 retains an LM 110 at a constant radial position with respect to the central axis and a constant circumferential position on the fictive tube 180, and slidable relative thereto. The constant radial position of a channel 510 is marked by distance r between the central axis 360 and the channel 510, which distance r is constant within the LM guide 300. The constant circumferential position is marked by angle a between an arbitrary radial line 364 and a radial line to the channel 510, which angle a is constant within the LM guide 300; the radial lines are centred on the central axis 360.

FIG. 7A is a detailed view of a channel into which a LM 110 is disposed.

FIG. 8 is a side view of a LM guide 300 that is an articulated LM guide 305 having a disc shaped body 352, and a distal side 344 and a proximal side 342. A central axis (A-A') is indicated. The articulated LM guide 300 has a body 352 comprising at the distal side 344, one component of the pair of components that forms a pivot joint that is a dome protrusion 330, akin to the ball of a ball and socket joint. It further comprises at the proximal side 342, the other component of the pair of components that forms a pivot joint that is a reciprocating recess 340, akin to the socket of a ball and socket joint. Further indicated is a pair of rotation limiters (332, 332') fixedly connected to the dome protrusion 330, which are radial protrusions from said dome protrusion 330. These couple with a pair reciprocating slots 334, 334' fixedly connected to the receiving recess 340 of an adjacent articulated LM guide (not shown), to prevent mutual axial rotation of adjacent articulated LM guides.

FIG. 9A is a plan view of a part of an LM guide 300 showing a channel 510 in detail together with dimensional indications that are the channel width 320 and channel height 322. The outer edge 356 of the LM guide 300 is also shown.

FIG. 9B is a side view of a part of an LM guide 300 of the invention showing a channel 350 in detail together with dimensional indications that are the channel width 320 and LM body thickness 328 which is equal to the channel thickness. The outer edge 356 of the LM guide 300 is also shown.

FIG. 10A is a plan view of a LM 110, together with dimensional indications that are the LM length 122 and LM width 124. A longitudinal axis (L-L') of the LM is also indicated.

FIG. 10B is a planar section of a LM at point B in FIG. 10A together with a dimensional indications that are the LM thickness 126 and LM width 124.

FIG. 11A is a plan view of a part of an LM guide 300 showing an open channel 350 in detail together with dimensional indications that are the channel width 320 and channel height 322. The outer edge 356 of the LM guide 300 is also shown.

FIG. 11B is a side view of a part of an LM guide 300 of the invention showing a channel 350 in detail together with dimensional indications that are the channel width 320 and LM body thickness 328 which is equal to the channel thickness. The outer edge 356 of the LM guide 300 is also shown.

Figure 12:
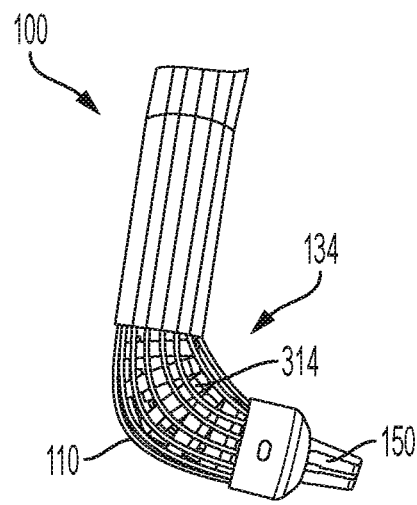
FIG. 12 is a photograph of a bent BDP where the LMs are disposed in LM guides having open channels.

FIG. 12 shows a view of a BDP 134 wherein the LMs 110 are disposed in LM guides 314 having open channels (as shown for instance in FIG. 11A). In the bent configuration, the LMs are lifted from the channels, thereby creating instability of the BDP.

Figure 13:
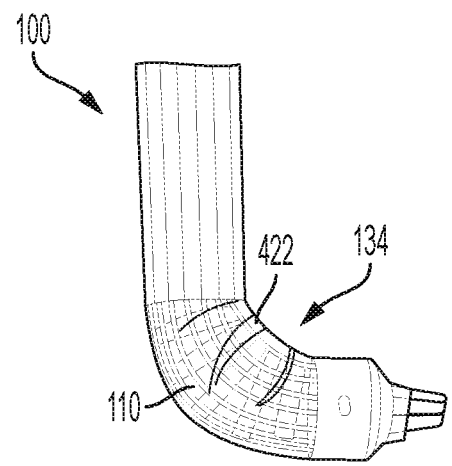
FIG. 13 is a photograph of a bent BDP disposed with a compliant sleeve, where the LMs are provided in LM guides having open channels.

FIG. 13 shows a view of a BDP 134 wherein the LMs 110 are disposed in LM guides having open channels (as shown for instance in FIG. 11A), and an attempt is made to retain them using a compliant sleeve 422 alone disposed over the BDP. The compliant sleeve does not prevent that in the bent configuration, the LMs are lifted from the channels, thereby creating instability of the BDP.

Figure 14:
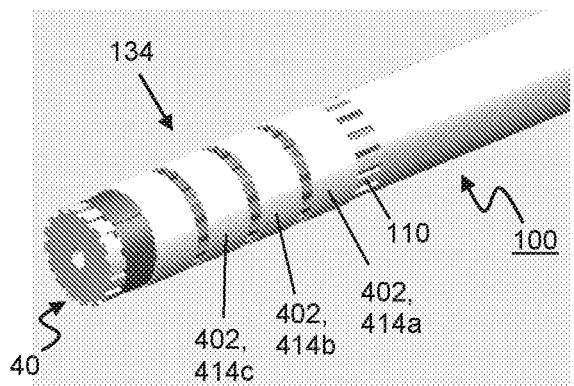
FIG. 14 shows an isometric view of a BDP in a straightened configuration wherein the LMs are disposed in LM guides having open channels, and a first component of a sheath unit that is a segmented tube is provided over the BDP.

FIG. 14 shows an isometric view of a BDP 134 wherein the LMs 110 are disposed in LM guides having open channels (as shown for instance in FIG. 11A). Disposed over the BDP 134 is a first layer of a sheath unit that is a segmented tube 402, wherein the individual segments (414a-c) are spatially separated and disposed across the regions. Note that the individual segments (414a-c) are not necessarily provided in the gaps between the LM guides—it suffices that they cover at least partially an LM guide and/or a gaps in the LM guides.

Figure 14A:
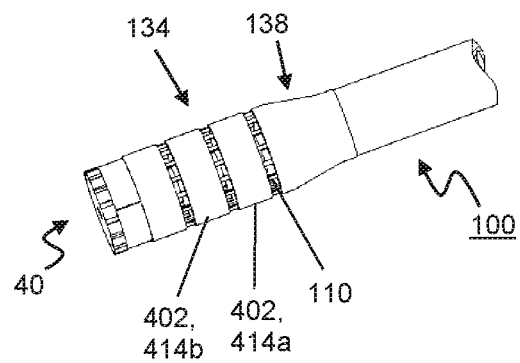
FIG. 14A shows an isometric view similar to that of FIG. 14, provided with a DAR.

FIG. 14A is similar to the FIG. 14 and is provided with a DAR 138 disposed adjacent to the BDP 134 and containing two segments (414a-b).

Figure 15:
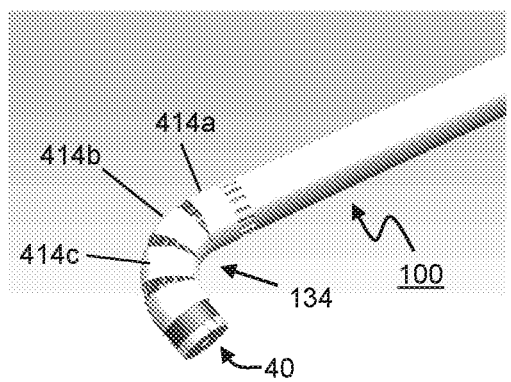
FIG. 15 shows an isometric view of the BDP of FIG. 14 in a bent configuration.

FIG. 15 shows an isometric view of the BDP 134 of FIG. 14 in a bend configuration. The individual segments (414a-c) are free to become more spaced apart on the longer (outside) edge of the curve, and more bunched together on the shorter (inside) edge of the curve.

Figure 15A:
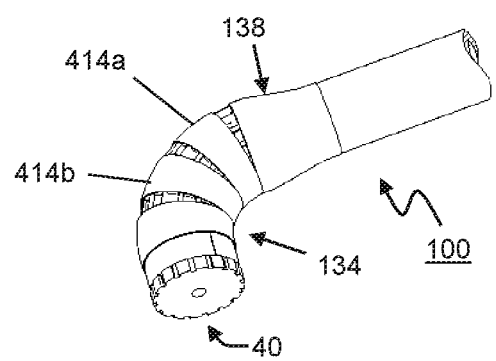
FIG. 15A shows an isometric view of the BDP of FIG. 14A in a bent configuration.

FIG. 15A is similar to the FIG. 15 and is provided with a DAR 138 disposed adjacent of he the BDP 134 and containing two segments (414a-b).

Figure 16:
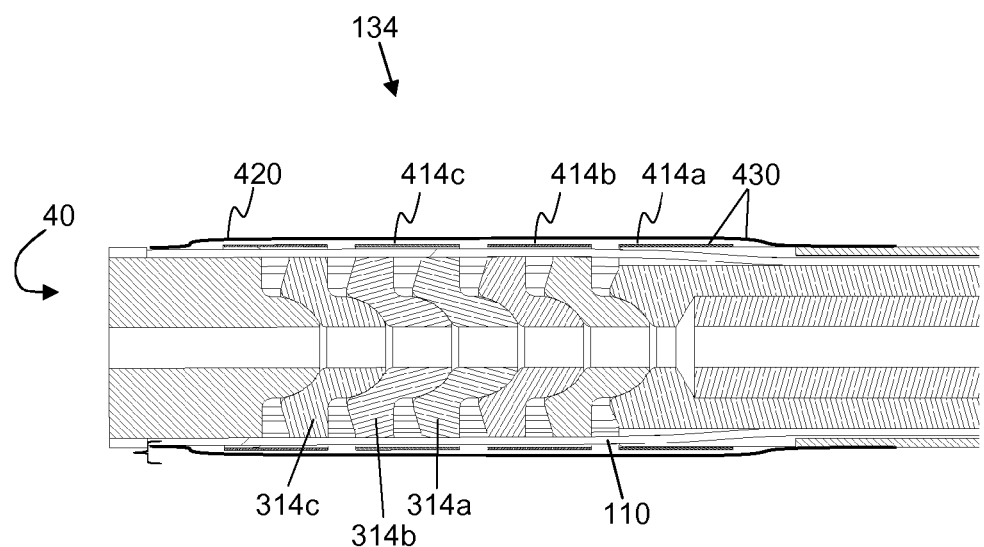
FIG. 16 shows an isometric view of a straightened configuration wherein the LMs are disposed in LM guides having open channels, and provided with a sheath unit.

FIG. 16 is a cross-sectional view of a BDP 134, showing the articulated LM guides 314a-c, provided with LMs 110. Disposed over the BDP 134 is a sheath unit (430) comprising first layer that is a segmented tube 410, of the individual unconnected segments 414a-c. The sheath unit further comprises a second layer that is a compliant tube 420. The compliant tube helps the individual unconnected segments 414a-c to return to their original positions after the bent BDP 134 is straightened.

Figure 17:
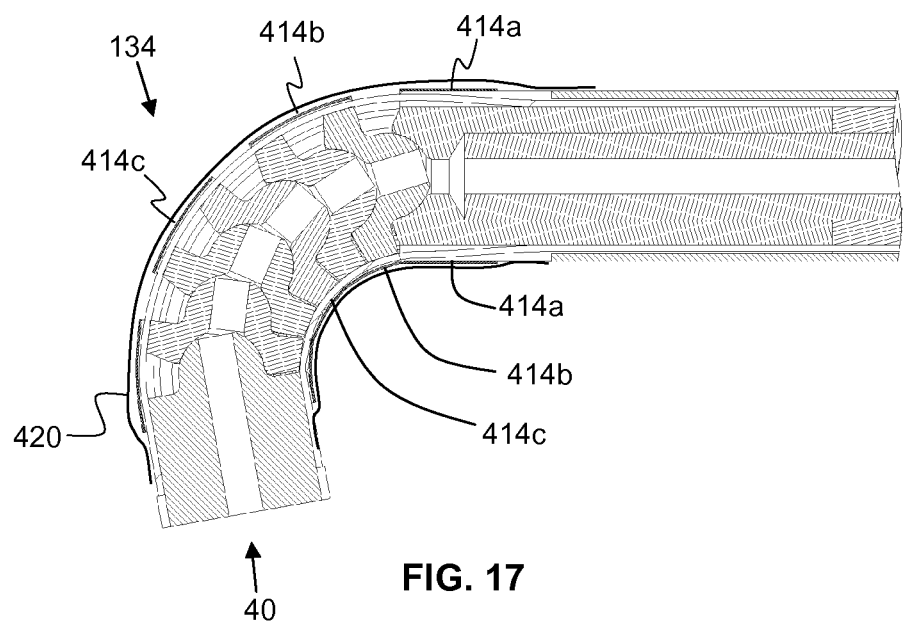
FIG. 17 shows an isometric view of a bent configuration wherein the LMs are disposed in LM guides having open channels, and provided with a sheath unit.

FIG. 17 is a cross-sectional view of the BDP 134 of FIG. 16 in a bent configuration.

Figure 18:
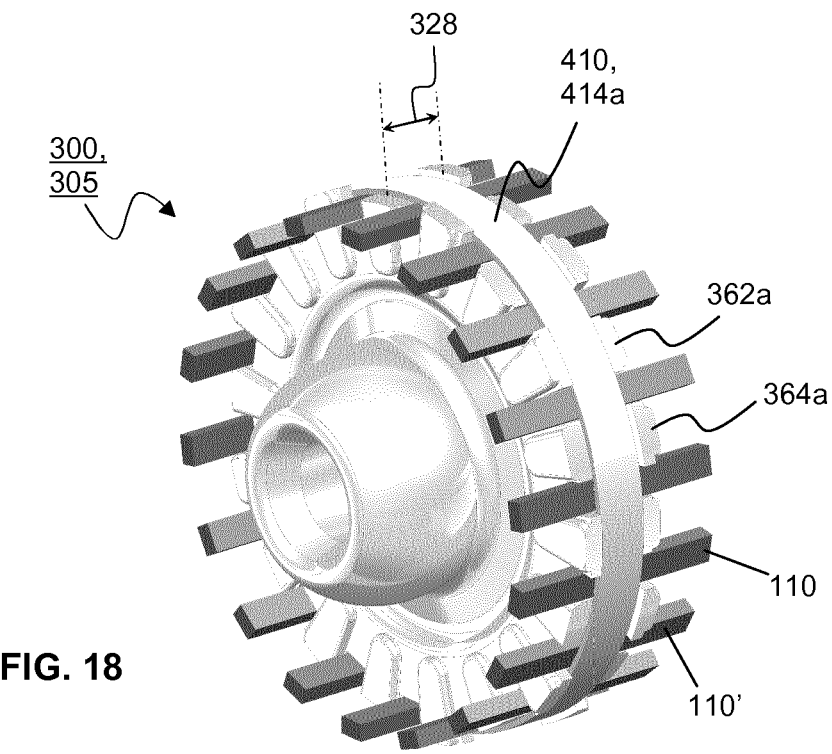
FIG. 18 is an isometric view of an LM guide that is an articulated LM guide disposed with a circumferential guide for the tube segment.

FIG. 18 is an isometric view of an LM guide 300 that is an articulated LM guide 305 disposed with a circumferential guide for the tube segment 414a. Also indicated is a width 328 of the LM guide 300 disc-shaped body.

Figure 19:
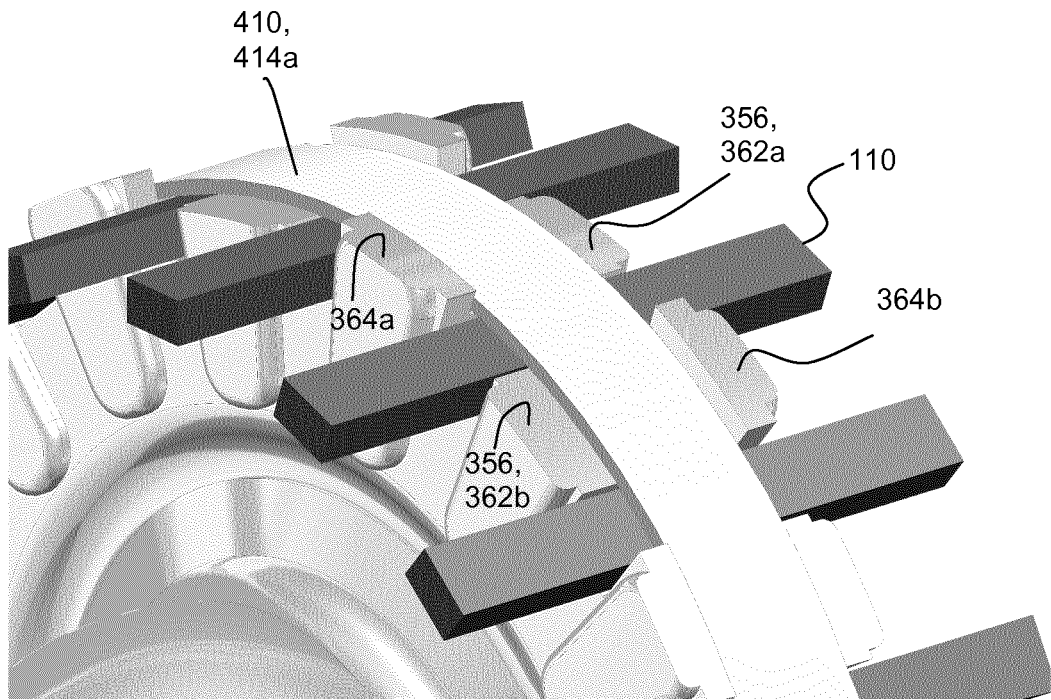
FIG. 19 shows a detail of FIG. 18.

FIG. 19 shows a detail of FIG. 18. The circumferential guide is formed from discrete protrusions 364a, b that project radially outwards from the circumferential outer edge 356 of the LM guide 305, and are disposed at discrete positions either side of the circumferential annular path. The discrete protrusions 364a, b are not aligned axially; each protrusion (e.g. 364a) aligns axially with the circumferential outer edge 356 (e.g. 362a) that is not disposed with a protrusion. It allows ease of manufacture in a two-piece mould; undercuts are avoided.

Figure 20:
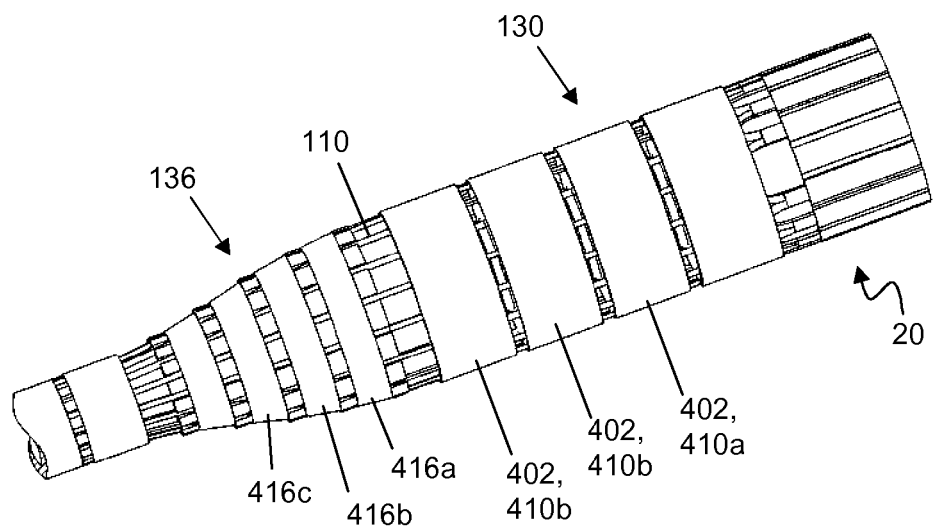
FIG. 20 shows an isometric view of a BPP and PAR, wherein the LMs are disposed in LM guides having open channels.

FIG. 20 shows an isometric view of a BPP 130 wherein the LMs 110 are disposed in LM guides having open channels (as shown for instance in FIG. 11A). Disposed over the BPP 134 is a first layer of a sheath unit that is a segmented tube 402, wherein the individual segments (410a-c) are spatially separated and disposed across the regions. Note that the individual segments (410a-c) are not necessarily provided in the gaps between the LM guides—it suffices that they cover at least partially an LM guide and/or a gaps in the LM guides. Also shown is the PAR (136) formed from a plurality of separate LM guides that each has a disc-shaped body, and a spacing joint separating the disc-shaped body, the channel of such LM guide being open-edged. To retain the LMs within the channels, a ring (416a-c) of flexible or foldable, non-radially compliant material disposed in each space separating the disc-shaped bodies.

FIG. 21 is a cross-sectional view of a BDP 134, showing the articulated LM guides 314a-c, provided with LMs 110, and a DAR 138. Disposed over the BDP 134 is a sheath unit (430) comprising first layer that is a segmented tube 410, of the individual unconnected segments 414a-c. The sheath unit 430 further comprises a second layer that is a compliant tube 420. The compliant tube helps the individual unconnected segments 414a-c to return to their original positions after the bent BDP 134 is straightened.

The invention claimed is:

1. A longitudinal steerable tool (100) having a proximal (20) and distal (40) end comprising:
   a set of longitudinal members (110, LMs) arranged in a longitudinal direction, and
   a bendable proximal part (130, BPP), bendable distal part (134, BDP), and a shaft region, SR (132) between the BDP (134) and BPP (130) wherein movements of the BPP (130) are transmitted to the BDP (134) along the SR (132) by the LMs (110),
   wherein the longitudinal steerable tool (100) comprises a sub-region that is a proximal amplifier region, PAR, (136) wherein the LMs (110) are arranged around a fictive tube (180) exhibiting size-decremental plane sections in a distal direction for at least 2 plane sections (182, 182') of the fictive tube (180), and
   wherein the longitudinal steerable tool (100) comprises a sub-region that is a distal attenuating region, DAR, (138) wherein the LMs (110) are arranged around the fictive tube (180) exhibiting size-incremental plane sections in a distal direction for at least 2 plane sections (184, 184') of the fictive tube (180).

2. The longitudinal steerable tool (100) according to claim 1, wherein:
   consecutive plane sections of the fictive tube (180) in the PAR (136) gradually decrease in size in the proximal (20) to the distal (40) direction, and/or
   consecutive plane sections of the fictive tube (180) in the DAR (138) gradually increase in size in the proximal (20) to the distal (40) direction.

3. The longitudinal steerable tool (100) according to claim 1, wherein:
   the PAR (136) is located at the proximal end (20) of the SR (132) or at least partially within the BPP (130), and/or
   the DAR, (138) is located at the distal end (40) of the SR (132) or at least partially within the BDP (134).

4. The longitudinal steerable tool (500) according to claim 1, further comprising a set of LM guides (300) configured to maintain the LMs (110) at the essentially constant circumferential and radial position and slidable with respect to the fictive tube (180).

5. The longitudinal steerable tool (100) according to claim 4, wherein:
   the PAR (135) is disposed with at least two of said LM guides (316, 316a-c), and/or
   the DAR (138) is disposed with at least one of said LM guides (318, 318a-c).

6. The longitudinal steerable tool (100) according to claim 4, wherein each LM guide (300) of the set comprises a body provided with a set of discrete channels (350) each accommodating one or two LMs (110), which channels are arranged around the fictive tube (180).

7. The longitudinal steerable tool (100) according to claim 6, wherein
the channels (350) of consecutive LM guides (316a-c) in the PAR (136) decrease incrementally in distance from a central (A-A') axis of the longitudinal steerable tool (100) in the distal (40) direction, and/or
the channels (350) of consecutive LM guides (318a-c) in the DAR (138) increase incrementally in distance from a central (A-A') axis of the longitudinal steerable tool (100) in the distal (40) direction.

8. The longitudinal steerable tool (100) according to claim 4, wherein at least some of LM guides in the set are articulated LM guides (316a-c, 318a-c) tandemly arranged in the BPP (130) and in the BDP (134), each articulated with respect to an adjacent articulated LM guide (316a-c, 318a-c), thereby supporting bending of the LMs (110) in the BDP (130) and in the BPP (134).

9. The longitudinal steerable tool (100) according to claim 8, wherein the articulated LM guides (316a-c, 318a-c) are in pairwise mutual contact through a pivot joint.

10. The longitudinal steerable tool (100) according to claim 4, wherein one or more of the LM guides in the set are fixed LM guides (312a-c) tandemly arranged in the SR (132) and rotationally fixed with respect to each other.

11. The longitudinal steerable tool (100) according claim 1, configured to move the BPP (134) and BDP (130) omni-directionally.

12. The longitudinal steerable tool (100) according to claim 1, wherein:
the fictive tube (180) in the PAR (136) contains a truncated cone shape, the larger end disposed at the proximal (20) end,
the fictive tube (180) in the DAR (138) contains a truncated cone shape, the larger end disposed at the distal (40) end.

13. The longitudinal steerable tool (100) according to claim 1, wherein: the BDP (134) is configured for movement in at least two different intersecting planes responsive to the movements of the BPP (130), and
the longitudinal steerable tool (100) is further provided with an end effector (150) at the distal end of the BDP (134)
the longitudinal steerable tool (100) is configured such that the end effector (150) is rotationally fixed in relation to the BDP (134), and the end effector is rotatable when the BDP (134) is in a bent position, by a complementary rotation of the BPP (130).

14. The longitudinal steerable tool (100) according to claim 1, wherein:
the PAR (136) and/or DAR (138) is each provided with a set of LM guides (300) configured to maintain the LMs (110) at the essentially constant circumferential and radial position and slidable with respect to the fictive tube (180),
each LM guide (300) in the PAR (136) and/or DAR (138) comprises a body provided with a set of discrete channels (350) each accommodating one or two LMs (110), and being open to a circumferential edge (356) of the LM guide (300), which channels are arranged around the fictive tube (180), and
the PAR (136) and/or DAR (138) is each provided with at least one ring of non-radially compliant material disposed in a space separating the LM guides (300), configured to retain the LMs (110) within the open edged channels (350).

15. The longitudinal steerable tool (100) according to claim 14, wherein the ring is made from heat-shrink material.

16. A longitudinal steerable tool (100) having a proximal (20) and distal (40) end comprising:
a set of longitudinal members (110, LMs) arranged in a longitudinal direction around a fictive tube (180) maintained at an essentially constant circumferential and radial position with respect to the fictive tube (180) and being slidable relative to the fictive tube (180), and
a bendable proximal part (130, BPP), bendable distal part (134, BDP), and a shaft region, SR (132) between the BDP (134) and BPP (130) wherein movements of the BPP (130) are transmitted to the BDP (134) along the SR (132) by the LMs (110)
a set of LM guides (300) configured to maintain the LMs (110) at the essentially constant circumferential and radial position and slidable with respect to the fictive tube (180), wherein
the BPP (130) and/or BDP (134) is each provided with two or more articulated LM guides (310a-c, 314a-c) of the set of LM guides,
each articulated LM guide (300) in the BPP (130) and/or BDP (134) is provided with a set of discrete channels (350) each accommodating one or two LMs (110), and being open to a circumferential edge (356) of the LM guide (300), which channels are arranged around the fictive tube (180), wherein each channel is open-edged in a radial direction with respect to a circumferential edge of the body,
a sheath unit (430) is disposed at least partially over each of the BPP (130) and/or BDP (134), the sheath unit (430) having less compliance in a radial direction compared with an axial direction, and comprises a first layer having little or no compliance in a radial direction, and a second layer having compliance at least in an axial direction, the first layer comprises a segmented tube (410) of a non-radially compliant material optionally heat shrink material, and the second layer comprises a compliant tube (420) and is disposed over the first layer, optionally wherein the first and second layers are not bonded together,
a circumferential outer edge of the articulated LM guide (300) in the BPP (130) and/or BDP (134) is provided with a circumferential guide that defines a circumferential annular path in which a detached segment (414a) of the segmented tube (410) is retained.

17. The steerable tool (100) according to claim 16, wherein the circumferential guide is formed from discrete protrusions (364a, 364b) that project radially outwards from the circumferential outer edge (356) of the articulated LM guide (300), and is disposed at discrete positions either side of the circumferential annular path.

18. The steerable tool (100) according to claim 17, wherein discrete protrusions either side of the circumferential annular path at the same radial position of the articulated LM guide (300) are not aligned axially (A-A').

19. The steerable tool (100) according to claim 18, wherein each protrusion (364a) aligns axially at a radial position with the circumferential outer edge (356) of the articulated LM guide (300) that is not disposed (362a) with a protrusion.

20. The steerable tool (100) according to claim 16, wherein a detached segment (414a) of the segmented tube (410) is made from a heat shrink polymer.

* * * * *